United States Patent
Baltz et al.

(10) Patent No.: US 10,393,654 B2
(45) Date of Patent: *Aug. 27, 2019

(54) COMPACT SENSOR FOR MEASURING TURBIDITY OR FLUORESCENCE IN A FLUID SAMPLE

(71) Applicant: In-Situ, Inc., Fort Collins, CO (US)

(72) Inventors: Nathan T. Baltz, Boulder, CO (US); Steven Collin Sewell, Fort Collins, CO (US)

(73) Assignee: IN-SITU, INC., Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/682,109

(22) Filed: Aug. 21, 2017

(65) Prior Publication Data

US 2018/0143132 A1    May 24, 2018

Related U.S. Application Data

(63) Continuation of application No. 14/937,240, filed on Nov. 10, 2015, now Pat. No. 9,778,180.

(60) Provisional application No. 62/115,593, filed on Feb. 12, 2015, provisional application No. 62/115,466, filed on Feb. 12, 2015, provisional application No. 62/077,528, filed on Nov. 10, 2014.

(51) Int. Cl.
  *G01N 21/53* (2006.01)
  *G01N 27/07* (2006.01)

(52) U.S. Cl.
  CPC .......... *G01N 21/532* (2013.01); *G01N 27/07* (2013.01); *G01N 2201/068* (2013.01)

(58) Field of Classification Search
  CPC ............. G01N 21/0303; G01N 21/532; G01N 21/538; G01N 21/8507; G01J 1/1626
  See application file for complete search history.

(56) References Cited

U.S. PATENT DOCUMENTS

| 5,099,920 A | 3/1992 | Warburton et al. |
| 5,259,452 A | 11/1993 | Wittrisch |
| 5,440,126 A | 8/1995 | Kemsley |

(Continued)

FOREIGN PATENT DOCUMENTS

| EP | 1851537 A2 | 9/2013 |
| WO | WO 2006/088829 A2 | 8/2006 |
| WO | WO 2014/125457 A1 | 8/2014 |

OTHER PUBLICATIONS

"6-Series Multiparameter Water Quality Sondes", *YSI Environmental*, 14 pages (Aug. 24, 2006).

(Continued)

*Primary Examiner* — Dominic J Bologna
(74) *Attorney, Agent, or Firm* — Leydig, Voit & Mayer, Ltd.

(57) ABSTRACT

Provided are turbidometers and fluorometers having a unique form-factor to accommodate a number of optical components in a confined geometry. This provides the ability to compensate for change in light intensity from an optical source even in a closed-loop manner. The ability to package reference and signal detectors, along with a relatively large diameter LED light source in a confined geometry is particularly suited for applications requiring small-diameter sensors, such as multi-parameter sonde devices having a total diameter that is in the sub-two inch range.

38 Claims, 17 Drawing Sheets

(56) References Cited

U.S. PATENT DOCUMENTS

| | | |
|---|---|---|
| D371,517 S | 7/1996 | McKee et al. |
| 5,596,193 A | 1/1997 | Chutjian et al. |
| 5,820,416 A | 10/1998 | Carmichael |
| D418,073 S | 12/1999 | Kreutzer et al. |
| 6,157,029 A | 12/2000 | Chutjian et al. |
| 6,234,019 B1 | 5/2001 | Caldeira |
| 6,305,944 B1 | 10/2001 | Henry et al. |
| 6,677,861 B1 | 1/2004 | Henry et al. |
| 6,779,383 B2 | 8/2004 | Lizotte et al. |
| 6,798,347 B2 | 9/2004 | Henry et al. |
| 6,928,864 B1 | 8/2005 | Henry et al. |
| 6,938,506 B2 | 9/2005 | Henry et al. |
| 6,943,686 B2 | 9/2005 | Allen |
| 7,007,541 B2 | 3/2006 | Henry et al. |
| 7,138,926 B2 | 11/2006 | Henry et al. |
| 7,142,299 B2 | 11/2006 | Tokhtuev et al. |
| 7,470,917 B1 | 12/2008 | Hoang et al. |
| D616,314 S | 5/2010 | Akomolede |
| 7,832,295 B2 | 11/2010 | Rodriguez et al. |
| 7,900,528 B2 | 3/2011 | Vincent |
| 8,429,952 B1 | 4/2013 | Bringhurst et al. |
| 8,488,122 B2 | 7/2013 | Dong et al. |
| 8,514,066 B2 | 8/2013 | Harmon |
| 8,542,189 B2 | 9/2013 | Milne et al. |
| 8,555,482 B2 | 10/2013 | Metzger |
| 8,664,938 B2 | 3/2014 | Palassis |
| 8,797,523 B2 | 8/2014 | Clark |
| D750,990 S | 3/2016 | Ettlin |
| D755,655 S | 5/2016 | Scott et al. |
| D769,140 S | 10/2016 | Park |
| D787,962 S | 5/2017 | Scott et al. |
| D787,963 S | 5/2017 | Scott et al. |
| D787,964 S | 5/2017 | Scott et al. |
| 9,689,855 B2 | 6/2017 | Scott et al. |
| 9,778,180 B2 * | 10/2017 | Baltz .................... G01N 21/532 |
| D803,081 S | 11/2017 | Scott et al. |
| 9,835,554 B2 | 12/2017 | Scott et al. |
| 2003/0117623 A1 * | 6/2003 | Tokhtuev ............... G01N 21/53 356/338 |
| 2003/0148637 A1 * | 8/2003 | Henry .................... G01D 11/24 439/10 |
| 2007/0140921 A1 | 6/2007 | Mitchell |
| 2009/0158819 A1 | 6/2009 | Vincent |
| 2010/0321046 A1 | 12/2010 | Randall et al. |
| 2011/0023586 A1 | 2/2011 | Leyer et al. |
| 2011/0273165 A1 | 11/2011 | Palassis |
| 2011/0273710 A1 * | 11/2011 | Dong ..................... G01N 21/53 356/338 |
| 2012/0242993 A1 * | 9/2012 | Schick ............... G01N 21/0303 356/442 |
| 2012/0262618 A1 | 10/2012 | Weakly |
| 2012/0325018 A1 | 12/2012 | Roth, II et al. |
| 2013/0008466 A1 | 1/2013 | Karagoz |
| 2013/0090789 A1 | 4/2013 | DeDonato |
| 2014/0017143 A1 | 1/2014 | Clark |
| 2016/0139070 A1 | 5/2016 | Scott et al. |
| 2016/0139101 A1 | 5/2016 | Scott et al. |
| 2016/0146777 A1 | 5/2016 | McKee et al. |

OTHER PUBLICATIONS

Ott Hydrolab, "Hydrolab HL4 Multiparameter Sonde", [Available online at: http://hydrolab.com/hydrolab-hl4-multiparameter-sonde/] (May 6, 2014).

In-Situ Inc., "Aqua TROLL 600 Multiparameter Sonde", [Available online at:https://in-situ.com/products/water-quality-testing-equipment/aqua-troll-600-multiparameter-sonde] (Sep. 14, 2015).

In-Situ Inc., "Aqua TROLL 600 Product Information", [Available online at: https://in-situ.com/blog/introducing-the-aqua-troll-600-water-quality-platform-2/] (Sep. 21, 2015).

In-Situ Inc., AquaTROLL 600 Specification Sheet, [Available online at: https://in-situ.com/wp-content/uploads/2015/09/Aqua_TROLL_600_Spec.pdf] (Apr. 30, 2016).

In-Situ Inc., TROLL 9500 Multiparameter Sonde, [Available online at: https://in-situ.com/products/water-quality-testing-equipment/troll-9500-multiparameter-sonde/] (Apr. 1, 2015).

In-Situ Inc., "Water Quality Testing Equipment Products", [Available online at: https://in-situ.com/product-category/water-quality-testing-equipment/] (Apr. 1, 2015).

Ott Hydrolab, "Hydrolab DS5—Multiparameter Data Sonde", [Available online at: http://www.ott.com/products/water-quality/hydrolab-ds5-multiparameter-data-sonde/ (Oct. 2014).

Wikipedia, "Sonde", (Accessed Nov. 4, 2015).

Teledyne ISCO, "AQ700 Water Quality Multi-Parameter Sonde", 2 pages, (Sep. 2013).

YSI Inc., "EXO1 Multiparameter Sonde", [Available online at: http://www.ysi.com/productsdetail.php?EXO1-Water-Quality-Sonde-89] (Oct. 2014).

YSI Inc., "EXO2 Multiparameter Sonde", [Available online at: https://www.ysi.com/EXO2] (Oct. 2014).

Examiner's Report for corresponding CA Application No. 163113, dated Nov. 16, 2015, 3 pages.

International Search Report and Written Opinion corresponding to International Patent Application No. PCT/US2015/059918, dated Feb. 1, 2016, 8 pages.

International Search Report with Written Opinion corresponding to International Patent Application No. PCT/US2015/059920, dated Jan. 29, 2016, 7 pages.

International Search Report with Written Opinion corresponding to International Patent Application No. PCT/US2015/059925, dated Jan. 20, 2016, 8 pages.

International Search Report with Written Opinion corresponding to International Patent Application No. PCT/US2015/059939, dated Jan. 13, 2016, 9 pages.

* cited by examiner

COMPACT SENSOR FOR MEASURING TURBIDITY OR FLUORESCENCE IN A FLUID SAMPLE

CROSS-REFERENCE TO RELATED APPLICATIONS

This application is a continuation of U.S. patent application Ser. No. 14/937,240, filed Nov. 10, 2015, which claims the benefit of priority of U.S. Provisional Application Ser. Nos. 62/115,593 and 62/115,466 filed Feb. 12, 2015 and 62/077,528 filed Nov. 10, 2014, each of which are hereby incorporated by reference to the extent not inconsistent herewith.

BACKGROUND OF INVENTION

Provided herein are water quality instruments containing multiple sensors for measuring a plurality of water-related parameters. The sensors are uniquely configured to have an extremely high form factor so that they may be contained within a housing that minimizes dead space between sensors and within the housing, with the individual sensor ends forming a single continuous sensing surface. This provides a number of functional benefits in the field of multi-parameter sondes and related sensing methods, including for in-situ applications where the total diameter of the sonde instrument is desirably less than 4" or less than 2".

The sensors described herein include specially configured high-fidelity and robust turbidity sensors and fluorometers that may be incorporated into a multiparameter sonde, including any of those described in U.S. App. No. 62/077,528 filed Nov. 10, 2014 and U.S. Design application Ser. No. 29/513,888 filed Jan. 6, 2015, which are specifically incorporated herein by reference.

In contrast to the sensors provided herein, much of the existing state of the art in-situ turbidity sensors and fluorometers drift over time and temperature. Most designs use one light source and one detector, such as the systems described in U.S. Pat. No. 8,488,122. The disadvantage of such sensors arises from the light source, such as a light emitting diode (LED), whose brightness changes with temperature. Such change in optical output with change in temperature can show up as a false or erroneous change in the readings of the sensor. Methods exist for compensating for this change by measuring temperature and correcting the change in detector signal with temperature. This is time consuming, is not always accurate, and can be very non-linear, as LED optical output is generally non-linear with temperature.

Other state of the art in-situ turbidity sensors use one LED and two detectors, however, the two detectors are used to measure over two different optical path lengths to achieve a greater dynamic range of measurement. The shorter optical path length is optimized for measuring at high turbidity levels and the longer optical path length is optimized for measuring at low turbidity levels. Devices that measure at two optical path lengths generally require much larger sensor geometries unsuitable for sub-two inch sonde or multi-parameter sondes comprising multiple probes. The designs that work over a shorter path length to optimize range generally suffer from increased noise because of the much smaller excitation/detection volume due to noise statistics related to exciting and detecting in a smaller scattering volume.

The state of the art in-situ sensors generally do not have a built in reference detector and are considered "open loop". One reason for this is that the in-situ sensors typically have a limited amount of space in them and simply cannot accommodate the added detector in a reliable manner without unduly sacrificing dynamic range and/or signal-to-noise ratio. Usually temperature is measured to attempt to compensate for the LED output changes with temperature. When the LED output changes however, including for non-temperature related reasons, this method does not work. There are "closed loop" systems, but they are typically bulky on-line monitoring type analyzers, not suited for in-situ monitoring applications.

Conventional in-situ turbidity sensors do not have room for the additional optics and electro-optics described herein, especially for sub-2 inch sondes. State of the art sub-2 inch sondes typically have 4 removable sensors each usually between 12 and 16 mm diameter, including as described in U.S. Pat. No. 8,488,122. The round geometry of the sensors greatly limits the optics that can be squeezed into such a sensor.

In view of these limitations, there is a need in the art for fundamentally different optically-based sensor configurations and related optics and electro-optic components that can be tightly packaged for use in multi-parameter and sub-2 inch sondes. Provided herein are turbidity and fluorescent sensors having a fundamental change in structure to address the limitations of conventional sonde sensors, while providing fundamental benefits and attendant improved sonde reliability, durability, and sensitivity.

SUMMARY OF THE INVENTION

The disadvantages associated with the geometry and inability to reliably position desired optical components without sacrificing sensor performance is addressed herein by the use of a specially configured sensor having a sensing surface that is a portion of a circle, also referred generally herein as a "pie" type geometry. This geometry allows for a larger linear dimension inside the sensor to accommodate additional optics and electro-optics for performing real-time closed loop type corrections and compensation for variation in optical output that simply are not possible with conventional lay-outs. The sensors provided herein address and overcome these limitations by specially configuring integrated reference detector and beam splitter in a compact in-situ instrument for long term deployment, lower frequency of calibration and accurate monitoring independent of time, temperature and other environmental variables.

Provided are sensors and related methods that incorporate and integrate a beam splitter and a reference detector into a sensor having a compact form factor that can be used in a sub 2" sonde, including multi-parameter sondes having multiple sensors in a confined space. Some of the electro-magnetic radiation generated by a light source reflects off the beam splitter into a reference detector usually of the same type as the signal detector in the signal channel. The system measures both the signal and reference channel in parallel. The ratio, R=sig/ref is then computed. The ratio of the two measurements provides a much more stable reading, compared to that obtained from one signal detector. Any change in optical output due to temperature, such as an LED experiencing a change in temperature, affects the signal and reference by the same amount, so that the ratio of signal to reference remains constant with change in optical output intensity, thereby reliably accommodating a change in temperature.

The compact turbidity sensors provided herein are also configured to have a very short nominal optical path in water from the LED to the signal photodiode, while also maintaining a relatively large excitation/detection volume. This short path length and large excitation/detection volume allows the sensor to work over a wide dynamic range of turbidity while also achieving low noise turbidity measurements. This compact sensor easily achieves a 4000 NTU dynamic range, including up to 10,000 NTU, while also being very linear as compared to conventional turbidity analyzers, including a Hach® 2100 ANIS benchtop turbidity analyzer. "Dynamic range" refers to a turbidity range over which the sensor has good functional performance, including defined in terms of sensitivity or accuracy, or in terms of linearity of device output. In an aspect, any of the dynamic ranges provided herein include a lower turbidity range of 0 NTU, or other unit that signifies no detectable turbidity, such as between 0 to 4000 NTU, between 0 to 10,000 NTU, and any subranges therein.

Any of the sensors may include high index wedge window materials to ensure a compact design. Sapphire is a good high index choice because of its resilience to scratches. The LED wavelength for ISO 7027 Turbidity sensors is 860 nm+/−30 nm. The index of sapphire at this wavelength is about 1.7587. The ISO 7027 specifications requires nominally a detection at 90 degrees from the incident light. With high index optics the angle between the optical axis of the LED or emitter and the optical axis of the signal detector can be reduced thus allowing for a more compact geometry. For example with sapphire, the angle between the optical axes is about 64.8°. Other high index materials such as LASF9 glass which has an index of 1.8296 at 860 nm are also compatible.

The wedge windows are typically held in place using a water proof adhesive. In some cases it is advantageous to select an adhesive that has high transmittance at 860 nm and use this adhesive to both hold the wedge window in place and also to encapsulate or pot the volume behind each window. This helps minimize the effects of water ingress on the measurements.

Also provided herein are fluorimeter type sensors that also use wedge windows, but do not require the same 90° geometry as do the ISO 7027 type turbidity sensors. Using high index wedge materials, for example, in the excitation path can improve the sensor efficiency because the light doesn't bend away from the normal at the air/sapphire interface. With a sapphire wedge adhered to a sapphire window with the correct angles, the air/sapphire interface can be made such that the light hits normal to this interface. The subsequent light at the sapphire window/water interface bends such that the light is closer to the detector, than if a sapphire wedge was not used. Wedges in the excitation path will tend to improve efficiency more than wedges used in front of the detector that detect emitted light, because the emission statistics are Lambertian (equal probability of emission at all solid angles aka isotropic).

Using one sapphire window over both the emitter and detector holes can be advantageous because it makes cleaning the window more effective, as there are no crevices for unwanted biological growth or that catch when wiping or brushing for sensor maintenance. It also makes it easier to apply adhesive between the one sapphire window and the end cap, without as much concern for the adhesive flowing into the optical path. One potential disadvantage is light "bleed" through internally to the sapphire window with resultant increase in background signal. The design can, therefore, also include a light trap in an end cap that attenuates any internally reflected excitation light. This reduces the background signal. The light trap can be a machined notch or integrated into the mold. Another light trap may not involve using a dark hole such as a machined notch, but rather employ a pressure sensitive adhesive (PSA) with one side coated with an ultrablack coating. Stray light control kits which are PSA's that adhere to various surfaces to reduce unwanted reflected light are available, such as by Acktar Inc. The fluorometer sensor may also benefit from adhering the ultrablack PSA coatings to other locations such as on the signal detector optical window forming an annulus around the sensitive die area.

For either type of turbidimeter and fluorometer sensor, however, beam splitters may be used to improve the stability of each type of instrument. The beam splitter substrate can be made of any number of different materials including but not limited to quartz, BK7, sapphire and LASF9 glass. The beam splitter can be either coated or uncoated. The index difference between the air and substrate can many times provide sufficient reflectance into the reference channel. If more reflectance is desired than, coated beam splitter plates can be used which are usually specified at 50/50 or 30/70 or 10/90 beam splitters. Usually a coating on one side provides the split ratio. The second side of a plate beam splitter can be either coated or uncoated. If it is coated, the thin film interference coating usually is an anti-reflective (AR) coating to prevent reflections off the second surface.

Use of beam splitters and a reference detector also normalizes the calibration, so that calibrations are more consistent across sensors. This can reduce typical factory calibration requirements as the sensors are inherently calibrated by virtue of the instant design. For example, two turbidimeter sensors whose LED's differ by a factor of two in optical power output would have the same calibration, assuming all other optics are the same. This is because the ratio of the signal and reference independent of the LED intensity.

The aperture in front of the reference photodiode is another variable that can be adjusted to either increase or decrease the amount of light that comes to the reference detector. Another option to adjust light intensity is to add optical attenuators also known as neutral density filters. Adjusting the aperture is generally preferred however, because it avoids use of another loose component. The aperture can be adjusted so that the trans-impedance gains of each amplifier are made the same. In this manner, the trans-impedance stages are matched and thus track each other more accurately over temperature.

The techniques provided herein are also robust to thermal transients and do not drift over time, such as when the LED optical output power declines. This gives the sensor better long term stability with very low drift. Currently state of the art instruments can show as much as 2% drift per year due to LED dimming. In contrast, in an embodiment provided herein the sensors drift less than 0.5% per year due to LED dimming.

The sensors provided herein also have improved accuracy at high turbidity levels. The choice of components, especially LED's with integrated lenses and detectors with integrated lenses and filters, also facilitate making the sensor desirably compact.

Another important attribute of the instant invention is a sensor guard which allows fluid flow through the sampling area while still providing a consistent geometry in the optical path of the turbidity sensor. This allows for prediction, to a certain degree, of the amount of light scattering, particularly in low turbidity environments. Light that is not reflected by the solution being measured is referred herein as "stray light" which can bounce off of other surfaces or material outside the sonde, and can return to the detector causing errors in readings. A sensor guard provided herein creates a constant surface in the optical path which will scatter, reflect or attenuate the stray light. Black coatings, such as Teflon™ coating, can also be applied to the inside of the guard to attenuate light that hits the guard, thus even further reducing effects of stray light, including on threaded connections that provide connection of sensor guard to the base. Conventional guard designs, in contrast, have a variability based on how the restrictor or guard is oriented relative to the detector.

Any of the sensors described herein may be used as part of a sub-2-inch sonde, wherein the outer diameter of the sonde is less than or equal to 2 inches. The sonde may be a multi-parameter sonde comprising up to four independent sensors. The fluorometers provided herein may be used to measure fluorescence parameters associated with a fluorescent material, such as Rhodamine WT, Chlorophyll, and BG Algae. Any of the sensors described herein may also be configured to be stand-alone sensors.

Provided herein is a sensor for measuring turbidity or fluorescence comprising: a distal sensing end comprising: a vertex region; a first surface extending from said vertex region and ending at a first surface end point; a second surface extending from said vertex region and ending at a second surface end point, wherein said first surface and said second surface extend in different directions to form a vertex angle at said vertex region; a convex-curved outer surface that extends between said first surface end point and said second surface end point; a distal sensing surface defined by edges of said first surface, said second surface, said vertex region, and said curved outer surface; wherein a separation distance between said first surface end point and said second surface end point defines a maximum straight line distance on said distal sensing surface; a distal sensing end volume formed by said vertex region, said first surface, said second surface and said curved outer surface, thereby defining a cross-sectional area and shape of the volume, wherein the volume can be calculated by multiplying the cross-sectional area by a longitudinal length in which the relevant components of the optical system are located; an optical system positioned in said distal sensing end volume comprising: an optical source to generate a beam of electromagnetic radiation; an emission window through said distal sensing surface in optical communication with said beam of electromagnetic radiation and configured to pass at least a portion of said beam of electromagnetic radiation from said distal sensing end volume through said distal sensing surface to a sample volume adjacent to said distal sensing surface in an excitation direction; and a collection window through said distal sensing surface configured to pass at least a portion of an incoming beam of electromagnetic radiation in a collection direction to said distal sensing end volume; and a signal photodetector configured to detect said beam of incoming electromagnetic radiation in said collection direction; wherein said optical system is positioned in an optical plane that extends substantially perpendicular to said distal sensing surface and that is substantially aligned with a line corresponding to said maximum straight line distance.

The optical system may further comprise a beam splitter positioned in optical communication with the light source; and a reference photodetector to detect electromagnetic radiation reflected by the beam splitter.

The distal sensing surface may have a surface area that is less than or equal to 4 cm$^2$ and a maximum straight line distance that is greater than or equal to 2.3 cm, or a surface area that is between 3.2 cm$^2$ and 3.9 cm$^2$, and a maximum straight line distance that is greater than or equal to 2.5 cm and less than or equal to 3.1 cm. The vertex angle may be greater than or equal to 30° and less than or equal to 180°. In this manner, the number of independent sensors in a multi-parameter sonde may be as many as six, each having an angle of about 30°, or as few as two, each having a vertex angle of 180°, with the two semi-circular shaped sensors together forming a circle.

The sensor outer surface may have a curve defined by a radius of curvature, such as less than or equal to 3 cm.

The optical system may positioned within a length L from said distal sensing surface, with a corresponding volume then less than or equal to L*A, where A is the cross-sectional area of the distal sensing end and L the length down the sensor in which the optical system is positioned. L may be less than or equal to 5 cm, less than or equal to 4 cm, less than or equal to 3 cm, between 1 cm and 5 cm, or between 1 cm and 4 cm.

The optical source and photodetector are configured to provide a sensing height from the distal sensing surface of between 1 mm and 3.6 mm and a sensing volume of between 10 mm$^3$ and 30 mm$^3$. Of course, some variance to these dimensions are tolerated by the sensors provided herein. For example, this sensing volume refers to the subregion within the guard sensor volume through which light is intentionally directed and is intentionally detected. By varying the light beam cross-section and/or detector or window area, this sensing volume can correspondingly vary. Similarly, the optical source and photodetector are configured to provide a nominal optical path length between the optical source and the photodetector in water, via the sensing volume. This nominal optical path length may be between 4 mm and 10 mm.

The sensors provided herein are particularly suited for use in up to very turbid liquids, such as up to 10 NTU. Accordingly, the sensor may have a dynamic range that spans up to 10,000 NTU, including between 0 to 4,000 NTU.

The sensor may be further described as having a first surface and a second surface that are flat-faced, with the sensor configured for insertion into a multi-parameter sonde comprising a plurality of independent sensors, wherein the sensors in combination provide a substantially circular cross-sectional footprint. Flat-faced refers to a surface formed from a plurality of sensors that has minimal recess features, such as crevasses, including only minimal cracks associated with tight-fit contact between adjacent flat sensor housings. Accordingly, such crevasses may be described as occupying less than 5%, less than 1% or less than 0.5% of the total sum of end surface contact areas, or alternatively, a gap thickness between adjacent sensors that is less than 3 mm, less 2 mm, or less than 1 mm. Other conventional sensors, in contrast, may have large separation distances between sensors, such as greater than 1 mm, 2 mm, 3 mm, 5 mm or 1 cm.

The vertex region may comprise a notch for accommodating at least a portion of a drive shaft, such that when all sensor housings are connected, a cylindrical passage is formed for receiving a drive shaft that may then be used to rotate a wiper or brush to prevent biological growth on the distal sensing end and ensure optical windows remain optically transparent.

The distal sensing end volume has a cross-sectional shape formed by: the first inner surface and said second inner side that are straight-line linear having a length that is greater than or equal to 1.5 cm and less than or equal to 3 cm, and form a vertex angle with respect to each other that is greater than or equal to 30° and less than or equal to 60°; an outer surface having a shape that is curved; and an interior-facing vertex side that is curved for accommodating a portion of a rotatable drive shaft.

The sensor is compatible with various optical sources, such as light emitting diode (LED), a laser diode, a fiber optic light source, and a miniature lamp. The optical source may be a LED having a diameter that is greater than or equal to 5 mm, reflecting the advantageous geometry of the sensors provided herein. Depending on the size of the sensor housing, including the maximum linear distance, the LED may have an upper limit of 1 cm, 2 cm or greater.

The beam splitter may comprised of a material selected from the group consisting of: sapphire, LASF9 glass, quartz, BK7, clear plastic, polycarbonate, cyclic olefin copolymer and acrylic. The beam splitter may have a top surface facing the emission window and a bottom surface facing the optical surface, wherein one or both of said top and bottom surfaces are coated with an optical coating layer. The optical coating layer may be a thin film interference layer.

The sensor is compatible with a number of different photodetectors, such as a photodiode.

Optionally, an adjustable aperture may be optically connected to the reference photodetector to control light intensity to the reference photodetector.

As desired, other optical components may be used, such as one or more optical filters for controlling wavelength of transmitted electromagnetic radiation, as well as optical sources and detectors having integrated lenses, filters, or lenses and filters.

The windows may comprise a window material selected from the group consisting of a refraction material having an index of refraction that is greater than or equal to 1.7 over a wavelength range between 820 nm and 900 nm. The window material may be sapphire; LASF9 glass, clear plastic, polycarbonate, cyclic olefin copolymer, or acrylic.

The sensor may be described as having an emission optical axis corresponding to an alignment direction of the optical source and a detection optical axis corresponding to an alignment direction of the signal photodetector, wherein an optical angle formed by the emission optical axis and the detection optical axis is less than 70°.

The sensor may further comprise a wedge window formed of a material having an index of refraction that is greater than or equal to 1.7 for a wavelength range that is between 820 nm and 900 nm, wherein the wedge window material is adhered or bonded to the emission window material or said collection window material. The window material may cover both the emission window and collection window, thereby further improving water-tight seal with the sensor housing. An end cap may be provided through which the emission and collection windows traverse, wherein the window material forms a crevice-free connection with the distal sensing end to facilitate surface cleaning and minimize unwanted biological growth during use in a liquid environment. As desired, a light trap connected to the end cap may be used to attenuate unwanted internally reflected electromagnetic radiation.

Any of the sensors described herein may further comprise: a sensor guard operably connected to the distal sensing end, wherein the sensor guard comprises an inner surface having a black coating that defines said sample chamber; a plurality of passages through the sensor guard for introducing a liquid sample to the distal sensing end; wherein the guard inner surface and plurality of passages are configured to provide an optically uniform surface to minimize effect of guard orientation on an intensity of said beam of incoming electromagnetic radiation. Various coatings that appear black in color may be used, so long as they are durable in water environments. One example of a suitable coating is a Teflon™ coating.

The sensor may have a ratio of light intensity detected by the reference detector and the signal detector to compensate for a temperature-induced variation in optical output from the light source, thereby providing temperature compensation without a temperature measurement. The ratio of light intensity detected by the reference detector to the light intensity detected by said signal detector may be independent of light intensity generated by the light source.

The sensor may be further described in terms of a number of quantifiable parameters. For example, having a long-term stability characterized by a sensor output drift that is less than 0.5% per year.

The surfaces of the sensor may be part of a sensor housing that is water-tight. Other layers may be used to improve the water-tightness, such as an encapsulating layer positioned over the distal sensing end. The encapsulating layer may be optically transparent, at least in the regions of the optical windows.

The sensor may be a turbidity sensor or a fluorescent sensor. The turbidity sensor may have a dynamic range of at least 4000 NTU, such as up to 10,000 NTU.

The sensor may further comprise a block that is optically opaque to visible light in which the signal and reference photodetectors are embedded, further comprising a light path through the block to provide optical communication between the light source and the signal and reference photodetectors.

Also provided herein are various methods of making or using any of the sensors provided herein. For example, a method of making a compact turbidity or fluorescent sensor may comprise the steps of: enclosing a plurality of optical components within a pie-shaped sensor housing having an outer surface shape that is a portion of a circle a first and second surface extending from a vertex region and connecting to ends of said outer surface shape, with a unique maximum straight line distance between the outer surface ends, and a distal sensing end volume in which the optical components are confined that is less than or equal to 20 cm$^3$. The lower limit, depending in part on the application and the ability to produce and detect desired optical intensity, may be greater than 1 cm$^3$, greater than 5 cm$^3$, or greater than 10 cm$^3$. The plurality of optical components comprise an optical source, a beam splitter, a reference photodetector, and a signal photodetector that are aligned with the unique maximum straight line. An emission window is provided through a distal sensing surface of the wedge-shaped sensor housing for passing electromagnetic radiation from the optical source to a sample chamber. A collection window is provided through a distal sensing surface of the sensor housing for collecting scattered electromagnetic radiation or emitted fluorescence radiation from the sample chamber to the signal photodetector. In this manner, a compact turbidity or fluorescent sensor is provided, including for use with a multi-parameter sonde.

Also provided is a method of measuring turbidity or fluorescence in a fluid sample by providing any of the sensors described and introducing a fluid sample to the distal sensing end. Electromagnetic radiation is introduced to the fluid sample from the optical source. A reference light intensity is detected with the reference photodetector and a signal light intensity detected with the signal photodetector. A ratio of the reference and signal light intensity is calculated, thereby measuring turbidity or fluorescence in the fluid sample.

For aspects where the sensor is used to measure turbidity in accordance with ISO7027, the excitation direction and the collection direction may define a measurement angle that is within 5°, within 2°, within 1° of a right angle, or that is a right angle. This requirement may be relaxed for fluorescent sensors.

Any of the sensors herein may have an optical system that further comprises: a beam splitter positioned in optical communication with the light source; and a reference photodetector to detect electromagnetic radiation reflected by the beam splitter.

Also provided herein are methods of making any of the sensors described herein and methods of using any of the sensors described herein.

Any of the sensors provided herein are compatible with and satisfy the requirements of the ISO 7027 determination of turbidity technique, including for in situ applications where the sensor is immersed at the location being monitored. This is in contrast to bench-top analyzers where the fluid sample is removed from the environment and introduced to the analyzer.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
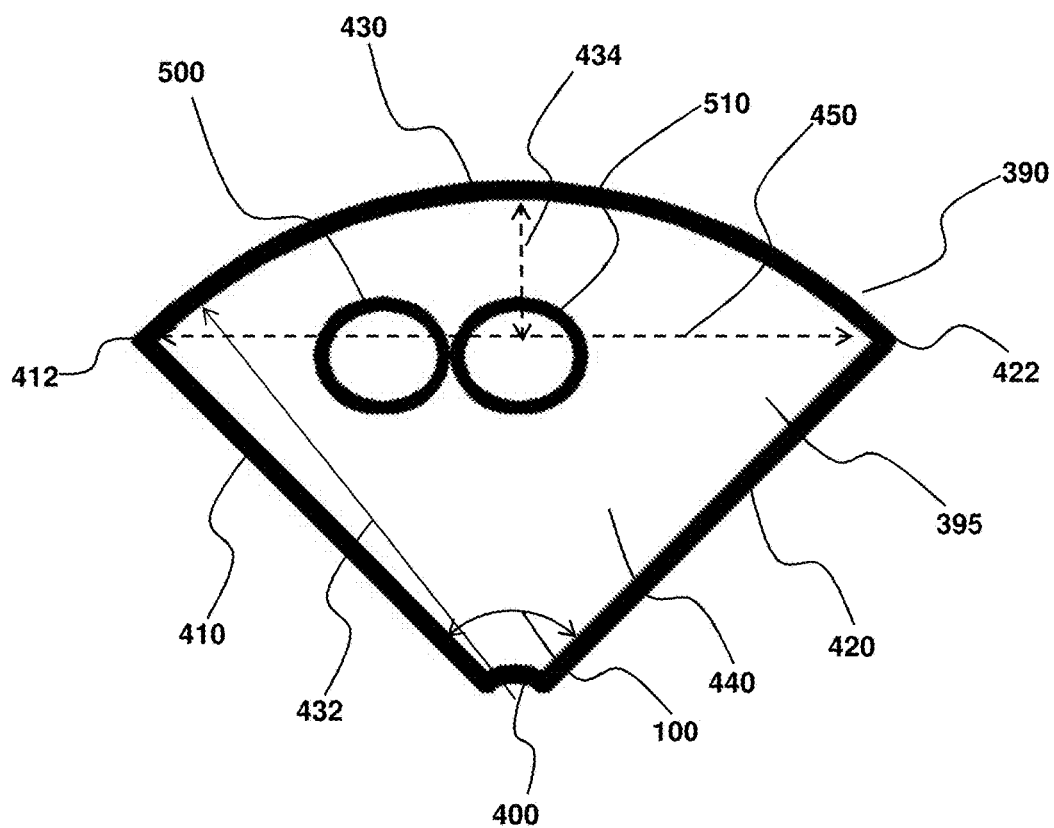
FIG. 1 is a top view of a turbidity sensor showing the distal sensing surface and windows therethrough.

In general, the terms and phrases used herein have their art-recognized meaning, which can be found by reference to standard texts, journal references and contexts known to those skilled in the art. The following definitions are provided to clarify their specific use in the context of the invention.

"Sonde" refers to a water quality monitoring instrument. "Multi-parameter" sonde refers to a sonde having multiple independent separate sensors for providing multiple water parameter values.

"Independent sensors" refers to the ability to insert or remove a sensor without affecting other sensors. For example, one of the sensors may be removed and replaced with a sensor blank. Similarly, a user in the field may simply remove one independent sensor and replace it with another of the same or different sensor, without affecting the other sensors. "Sensor blank" refers to an equivalently shaped object that is used in place of a sensor. It is useful if the user does not need or have a sensor to connect to the base so as to fully fill the sensor guard.

The devices provided herein are compatible with a range of sensors beyond the turbidity and fluorescence sensors described herein, including sensors that measure conductivity, dissolved oxygen (DO), oxygen-reduction potential (ORP), pH, pressure, depth, level, ion selective electrodes for various ions, such as nitrate, ammonium and chloride, temperature and correspondingly shaped sensor blanks.

"Continuous distal sensing surface" refers to a plurality of independent sensors that are placed adjacent to each other to form a single surface that, to the naked eye or casual observer, appears continuous. The invention, however, does tolerate some separation distance, preferably less than 2 mm, less than 1 mm, or less than 0.5 mm. Tight-fit and tightly held are used herein in a similar manner, to reflect the minimal space between adjacent surfaces, in contrast to conventional systems that have rather large gaps and attendant large void volumes. Accordingly, adjacent distal sensing surfaces that "substantially contact" each other may refer to an open surface area between sensors that is less than 5%, or less than 1% of the surface area of the continuous distal sensing surface. Such small separation distances minimize biological growth and associated fouling during use, including by air pocket confinement such that liquid does not contact surfaces during use, thereby further minimizing growth. Any remaining growth can be addressed and removed with the wiper and is quickly and efficiently cleaned, in contrast to conventional sondes and sensors where substantial biological growth results in fouling with time-consuming and challenging to cleaning.

Unless defined otherwise, "substantially" refers to a value that is within at least 20%, within at least 10%, or within at least 5% of a desired or true value. Substantially, accordingly, includes a value that matches a desired value. Accordingly, an optical plane is considered substantially perpendicular to a distal sensing surface if it is within at least 20%, 10%, or 5% of perpendicular, or is perpendicular. Similarly, "substantially aligned" refers to a line that is within 20%, 10% or 5% of parallel, or is parallel, and offset by less than 10%, less than 5%, or less than 1% of the lineal distance, or in absolute terms, less than 5 mm, less than 1 mm, or less than 0.5 mm.

"Operably connected" refers to a configuration of elements, wherein an action or reaction of one element affects another element, but in a manner that preserves each element's functionality. For example, a wiper operably connected to a center support refers to the ability to move the wiper without impacting the functionality of the center support that supports the sensors in an interlocking configuration.

Similarly, "optically connected"" refers to a configuration of elements wherein electromagnetic radiation can pass from one component to another, but in a manner that preserves each component's functionality.

"Releasably connected" or "releasably connects" refers to a configuration of elements, wherein the elements can be temporarily and reliably connected to each other and, as desired, removed from each other without adversely impacting the functionality of other elements of the device.

Example 1: Sensor Housing Configuration and Form Factors

The sensors may generally be described as "pie shaped", and can have an interlocking feature that holds the sensors together. The interlocking feature can be a tongue and grove design that holds all the sensors to the center support that is operably connected to the wiper. This has a number of benefits, including enhancing impact resistance as the interlocking protects the sensors during a drop or impact in situations where the sensor guard is not installed. It also holds the sensors tightly together and makes sensor guard installation easier. Without the interlocking feature the sensors tend to splay out and have to be pushed together to install the tightly fitting sensor guard.

Referring to FIG. 1, a distal sending end 395 is illustrated from a top-view to show a sensor housing 390 comprising a vertex region 400 from which a first surface 410 and second surface 420 extend to first surface end point 412 and second surface end point 422, respectively. The first and second surfaces define a vertex angle 100. A curved outer surface 430 connects end points 412 422. The outer surface 430 is described as concave-curved to reflect the curvature extends outward from the interior of the distal sensing surface 440. The separation distance between end points 412 and 422 defines a maximum straight line distance 450 on the distal sensing surface. The concave-curved outer surface can be further described in terms of a radius of curvature 432 and/or a maximum outer surface separation distance 434 from maximum straight-line distance as indicated by notional line 450. The unique semi-circumferential-shape of the distal sensing surface provides a number of functional benefits with respect to optical system positioning and packaging. For example, an emission window 500 and collection window 510 can be aligned along the maximum straight-line distance 450. The windows provide optical communication between a sample positioned on top of the distal sensing surface 440 and optical components beneath the distal sensing surface, while maintaining a water-tight barrier. The optical components are further discussed in FIGS. 4-5 and 7 and Example 3 below, and can be similarly aligned or substantially aligned with respect to notional line 450 and separated from the outer surface with respect to notional line 434. "Notional line" refers to a line formed between end points, but that is not necessarily physically formed or drawn on the device.

The vertex region 400 may comprise a point contact from which surfaces 410 and 420 extend. In the illustrated embodiment, however, the vertex region comprises a curved surface to provide the ability, in combination with other sensors, to define a passage through which a rotatable drive shaft is positioned (see 182 of FIG. 17). Such a drive shaft may be used to rotate a cleaning element, such as a wiper or brush, over the surface 440 (and other sensor surfaces) during use. Accordingly, the surface 440 may be further defined by a vertex region having a curved surface, including a portion of a circular surface configured to receive a portion of a rotatable drive shaft having a diameter of between about 1 mm and 5 mm.

Figure 2A:
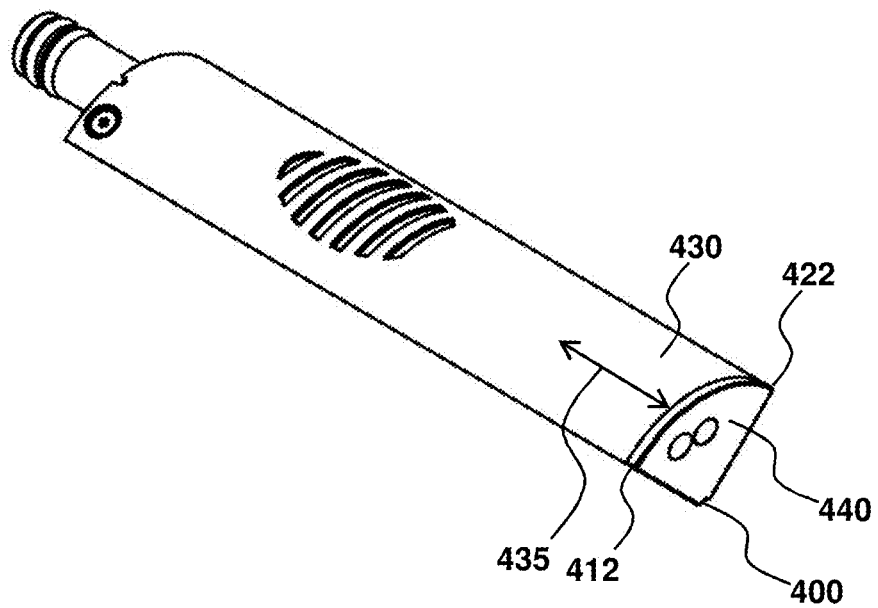
FIG. 2A-2D are different views of the sensor of FIG. 1.
Figure 2B:
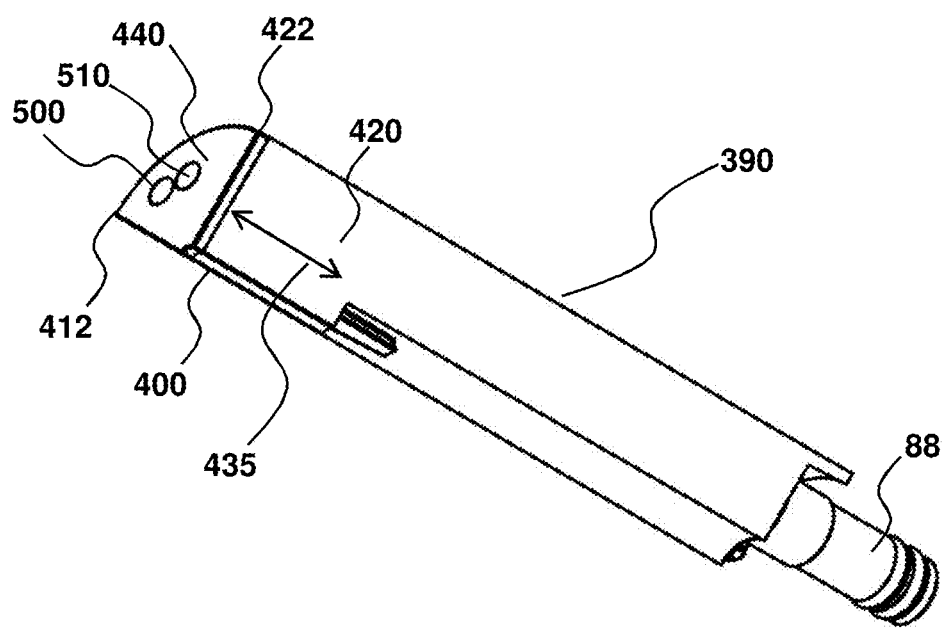
Figure 2C:
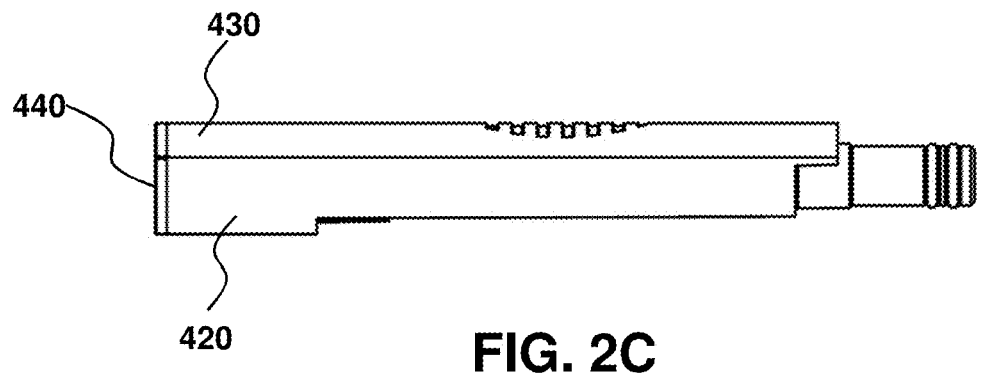
Figure 2D:
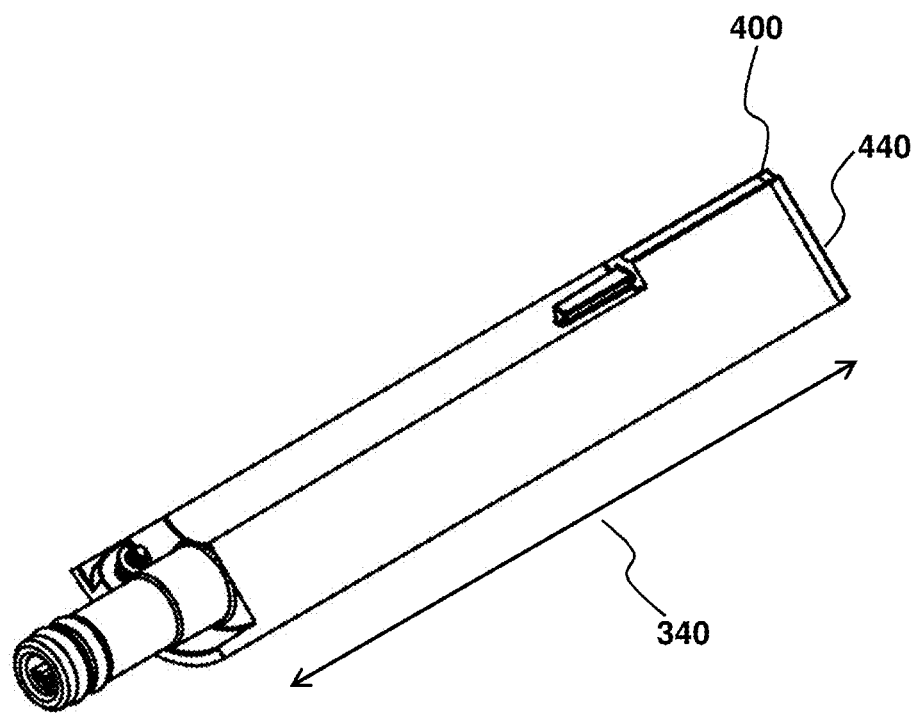

FIGS. 2A-2D are different views of the sensor of FIG. 1, to further illustrate an exemplary form-factor and geometry. FIG. 2A-2B are perspective views of the distal sensing end 435 and surface 440. As illustrated, the surface 440 corresponds to the plane formed by the most distal portion of the surface, whereas the distal sensing end defines a distal sensing end volume defined by the surface area of 440 and a distance from the surface, as indicated by arrow 435. These drawings better illustrate the shape of the various surfaces that have only one edge visible in FIG. 1, including the first 410, second 420 and outer 430 surfaces.

Depending on the sensor type, and more specifically the liquid parameter being measured, the distal sensing end or surface 440 will have different sensing elements. For the turbidity or optical sensors, elements observable with the distal sensing end or surface illustrated in FIG. 2B are an emission window 500 that passes light from the optical light source in the sensor housing to the sample volume adjacent to the surface 440; and a collection window 510 for directing desired scattered light or emitted fluorescent light from particles suspended in the fluid sample volume toward a signal photodetector in the distal sensing end volume.

As illustrated, the sensors may be provided with an interlocking mechanism to facilitate tight fit within a multi-parameter sonde. For example, a tongue extends from a notch end surface in a longitudinal direction that aligns with the sensor housing. A fastening member at the sensor proximal end may be used to connect the sensor to a sonde base, including to provide an electrical connection to the base to drive the opto-electronics within the housing.

Figure 16:
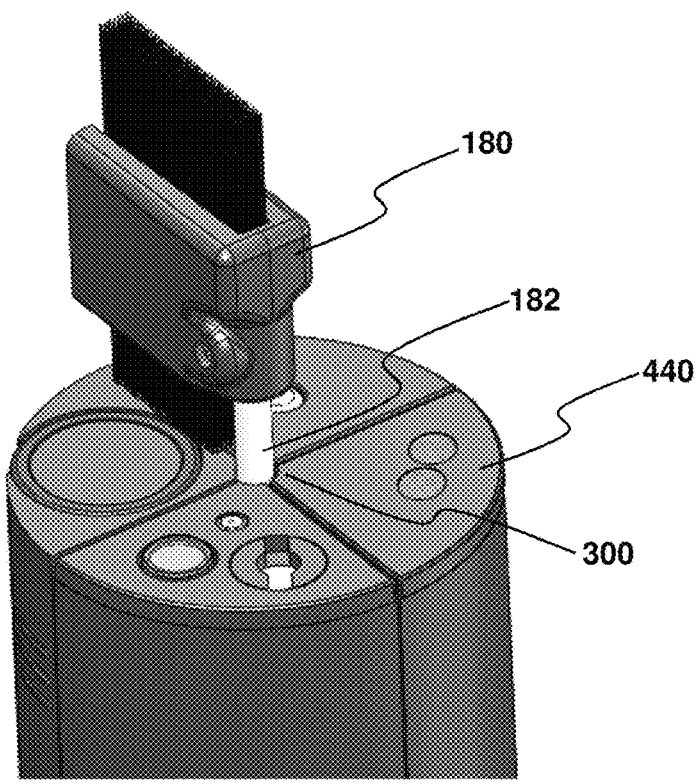
FIG. 16 is a close-up view of the continuous distal surface of the multi-parameter sonde, including a sensor for measuring turbidity or fluorescence, as described herein, with a wiper.
Figure 17:
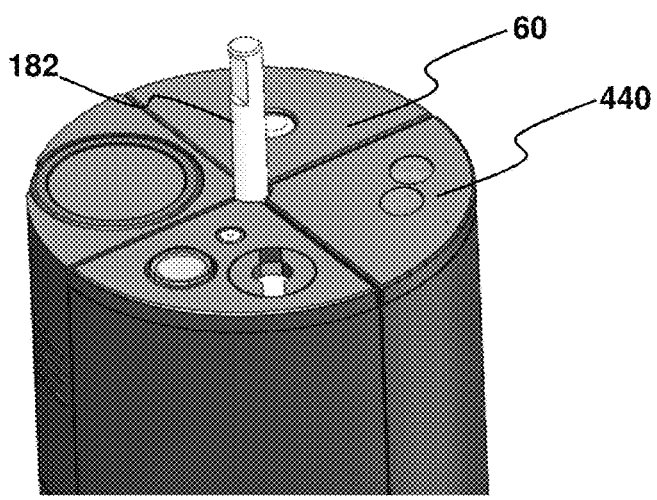
FIG. 17 shows the continuous distal surface of the multi-parameter sonde of FIG. 14B with the replaceable wiper removed, to better illustrate that the tight-fit between adjacent sensors leaves no observable spaces between the sensors, thereby improving cleaning action with the wiper, including over the turbidity or fluorescence sensor distal sensing surface.

Referring also to FIGS. 16-17, sensors with a vertex region curved surface or groove, in combination, form a central orifice 300 in which drive shaft 182 extends therethrough. The drive shaft rotates wiper 180 which is connected thereto.

The independent sensors may be further defined in terms of a longitudinal distance 340 (FIG. 2D) and a radial dimension 432 (FIG. 1).

Figure 3:
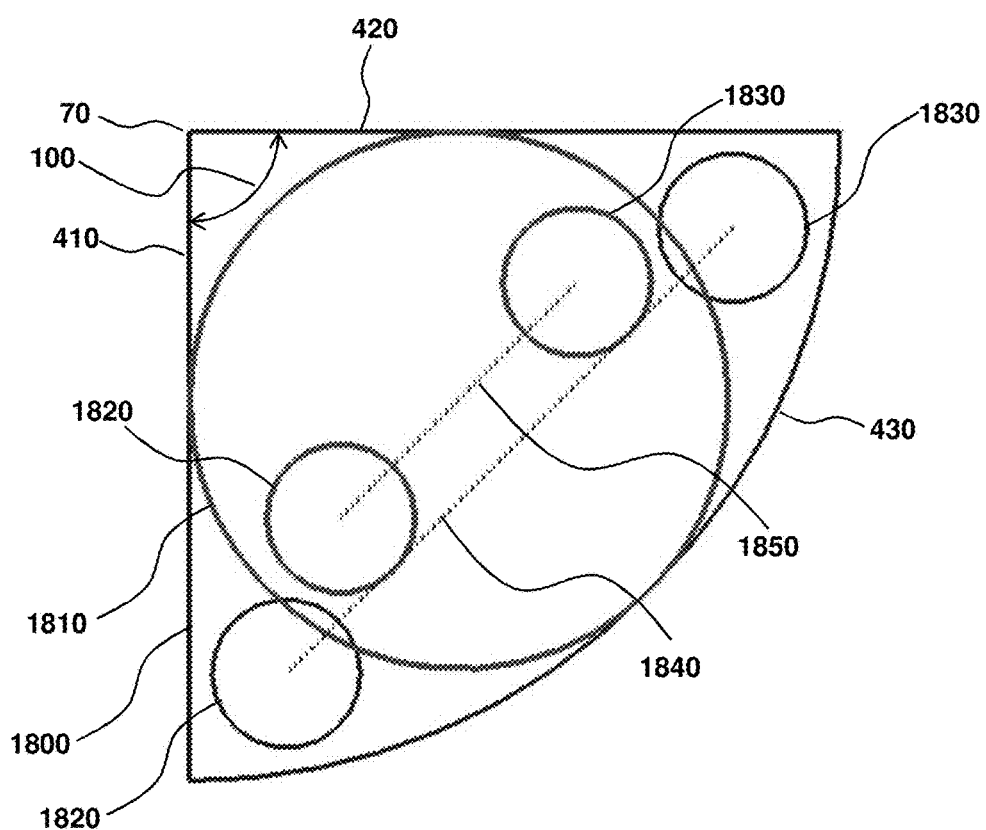
FIG. 3. Schematic illustration comparing the increased distal sensor surface area available to a one-quarter pie-shaped sensor compared to an equivalent circle-shaped sensor that can fit into an equivalent perimeter of the pie-shaped sensor.

The high-form factor sensors may also be described as pie-shaped, referring to a shape of the sensor cross-section having a corner with two-sides, and a curved outer surface. FIG. 3 shows an embodiment where the vertex angle 100 that defines the angle between sides 410 420 of a sensors are 90°, to provide a cylindrically-shaped high form factor sensor package such as for four independent sensors in a multi-parameter sub 2" sonde. This pie-shape, formed by side 410 420 and outer 430 surfaces, besides having benefit of being able to be tightly packed, also provides increased sensitivity, such as for optical-based sensors, as a result of the maximum separation distance along line 1840. A pie shaped sensor 1800 has an increased surface area of about 45% compared to an equivalently sized circular shaped sensor 1810 confined within the perimeter of the pie-shaped sensor, as indicated in FIG. 3. This permits optical spacing increase between emitting 1820 and receiving 1830 optics to be increased in the pie sensor by about 89% (compare separation distance 1840 with 1850) compared to conventional circular-shaped sensors, with attendant increase in sensitivity. Furthermore an integrated circuit and corresponding circuit board is configured to be positioned in a direction that is aligned with maximum separation distance line 1840, thereby maximizing width of the circuit board and allowing the circuit board to extend a length of up to longitudinal length illustrated by the arrow 340 of FIG. 2D and in alignment with the optical components described in Example 2 below.

Example 2: Optical Components in Distal Sensing End

Figure 4:
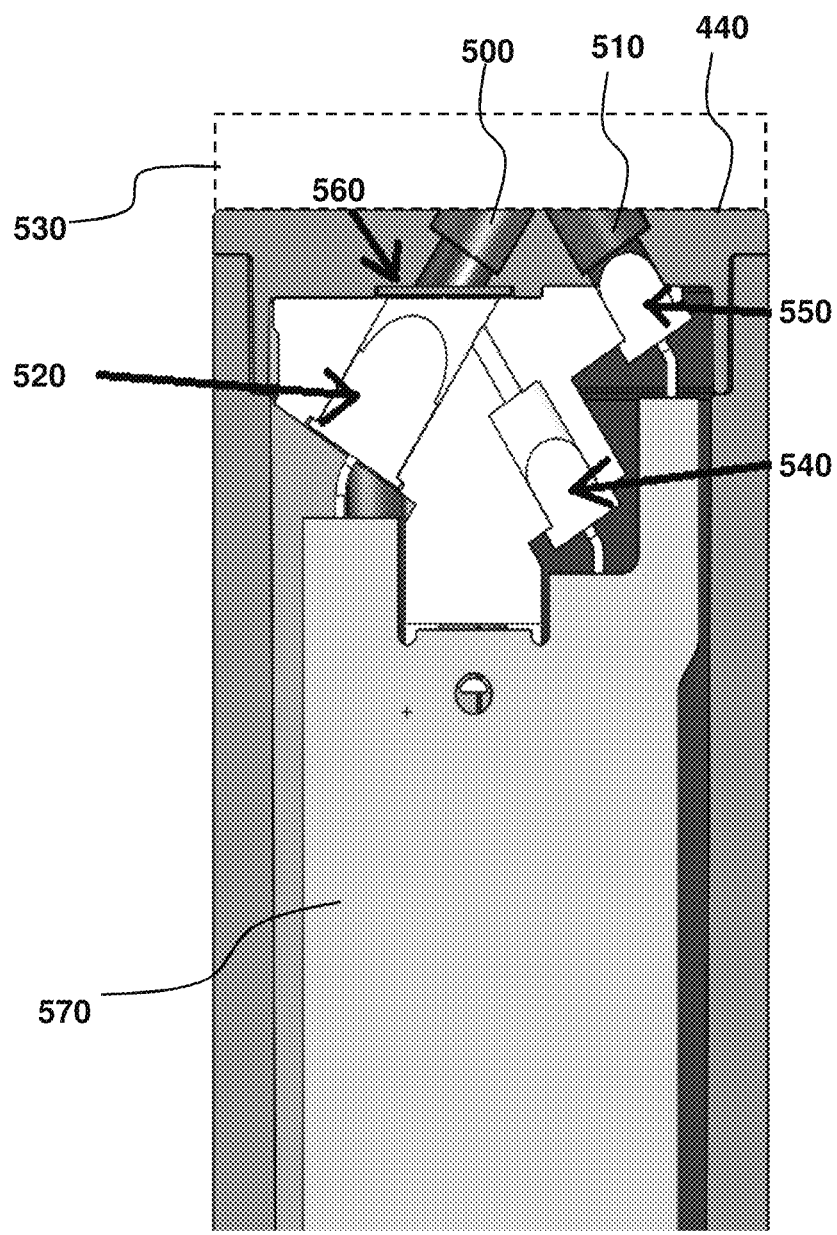
FIG. 4 is a cross-sectional view of a turbidity sensor with the optical system positioned in the distal sensing end volume, with an end cap connected to the sensor side walls.

Optical components positioned within the distal sensing end volume are schematically illustrated in FIG. 4. Optical light source 520, such as a large diameter (5 mm or larger) LED is optically connected to the emission window 500 for providing electromagnetic radiation generated by the light source to a fluid sample volume 530 positioned adjacent to the distal sensing surface 440. Also illustrated is reference photodetector 540 in optical communication with a portion of the electromagnetic radiation emitted from the light source 520 and signal photodetector 550 in optical communication with collection window 510 for detecting light transmitted through the collection window that is associated with scattering by or fluorescence of material in the fluid sample volume 530. A beam splitter 560 may be positioned in optical communication with the light source 520 to reflect a portion of the electromagnetic radiation to the reference detector 540 to compensate for variation in light output from the source, such as by a change in temperature, via ratio of light detected by signal detector 550 and light detected by reference detector 540. Various electronics may be provided on a circuit board 570 that extends across a width of the maximum separation distance 450 (FIG. 1) and down a length of the sensor housing as indicated by arrow 340 in FIG. 2D. Accordingly, the pie-shaped geometry also provides a benefit of facilitating placement of the circuit board within the housing, in a manner that naturally and substantially aligns with a line indicated by 450.

Figure 5:
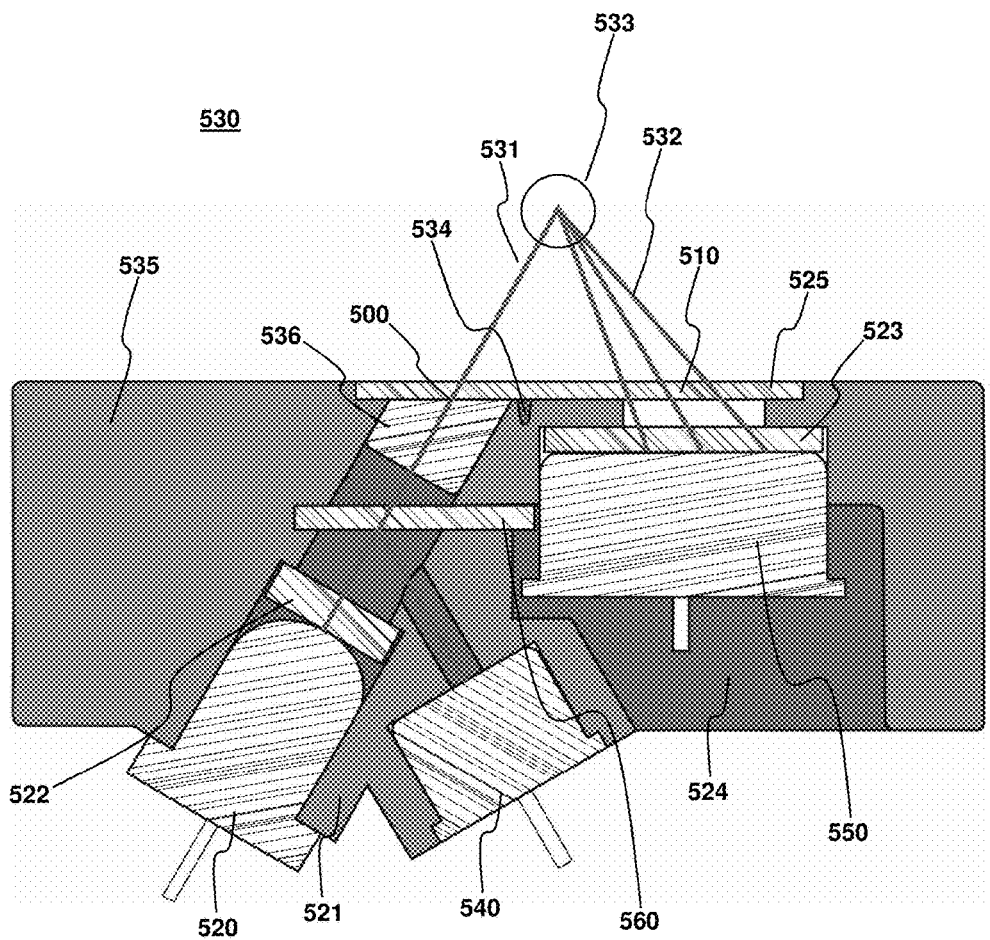
FIG. 5 is a cross-sectional view of a fluorometer or fluorescent sensor with optical components including a sapphire window, beam splitter, LED, signal and reference detectors and wedge optic.

A schematic illustration of the optical components for a fluorescent sensor is provided in FIG. 5, and is similar to the optical components outlined in FIG. 4, but does not require the detection optics be angled relative to the light source as the detector measures fluorescence and not optical scattering. Other optical components may be used, including appropriate excitation and emission filters for ensuring appropriate excitation wavelength is introduced to the fluid sample and appropriate emission wavelength is detected by the detector. A light trap 534 may be included to minimize interfering light. The distally-positioned optical components may be positioned within an end-cap 535, such as to provide a good water-tight configuration. As desired, the windows, beam splitter and wedge 536 may be formed from a material having a desired optical property, including index of refraction, such as sapphire. Any of the fluorescent and turbidity components, may be interchanged or incorporated with the other, as desired. For example, the light trap, end cap, window, wedge and/or filters 522 523 of FIG. 5 may be employed in the embodiment of FIG. 4, and vice versa. Other components in FIG. 5 include diode holder 521 that may hold a light source 520, such as a light emitting diode (LED), optical component head 524, sapphire window 525, sapphire wedge 536. Optical light path may be defined in terms of the light path 531 from the light source to fluid sample volume 533 and light path 532 from a suspended particle in the fluid sample volume to the signal detector.

In an embodiment, the detectors such as photodiodes, one or both of the signal and reference detectors, are embedded within an optical component head formed of a material that blocks light of the wavelength being detected. For example, the material can be opaque to block visible light, such as a black plastic. This allows the sensor to operate in full sunlight and also in all room light conditions without sacrificing accuracy or sensitivity and risking saturation. The material further assists in separating the light source from the detectors, so that unwanted stray light is blocked from the detectors. In an aspect, the optically opaque material in which the optical components are embedded is formed as part of the end cap, such as in which the windows, wedge(s), beam splitters and other optical components of interest are embedded.

Any of the optical sources provided herein are selected to provide good light output characteristics and may be selected from the group consisting of: a light emitting diode (LED), a laser diode, a Vertical Cavity Surface Emitting Laser (VCSEL), a fiber source, or a miniature lamp, such as an incandescent lamp. In an aspect, the light source is a LED, including a point source emitter providing desirable light collimation with an integrated lens, also referred herein as a "point source emitter". One example of such a point source emitter is by Marktech Optoelectronics (Latham, N.Y.), including the Marktech Point Source Emitter as described on the internet at: marktechopto.com/pdf/Point_Source_Emitter_Application_Notes_2012-1.pdf. marktechopto.com/pdf/Marktech_Point_Source_Products_2012-1.pdf. Such a point source LED is advantageous for satisfying ISO 7027 requirements and improving dynamic range by providing an output of electromagnetic radiation from the LED output surface rather than from the sides and attendant lack of collimation, as is common with conventional LEDs.

Example 3: Sensor Guard

Figure 6A:
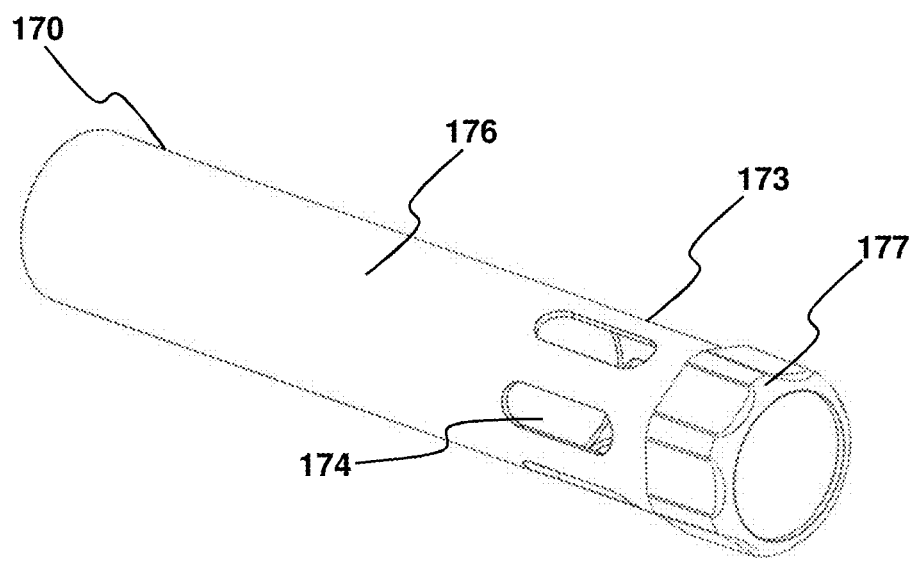
FIG. 6A is an illustration of a sensor guard configured for use with a multi-parameter sonde.
Figure 6B:
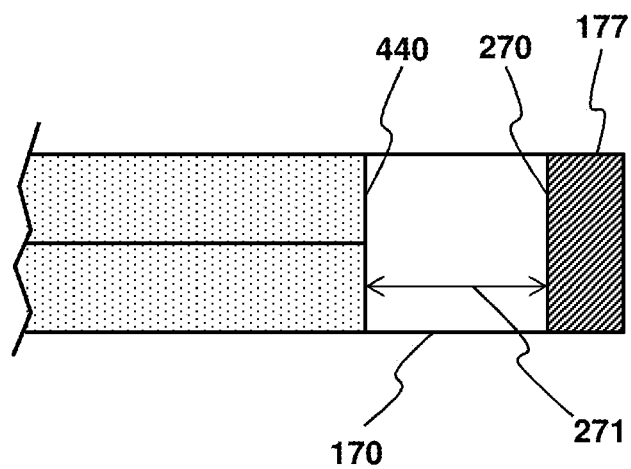
FIG. 6B is a cross-section of the sensor guard and sensors to illustrate configuration of a distal sensing end and sample volume.

The sensors provided herein may be used with a sensor guard, such as the sensor guard 176 of FIG. 6A having a plurality of passages 174 with interspersed solid guard sections 173. FIG. 6B is a sectional view along a central plane of the distal end of the sensor to the sensor guard cap 177 of sensor guard 170. An internal surface 270 of sensor guard cap 177 faces the distal sensing surface 60, and is separated by a sample distance 271. The sample distance 271 forms a corresponding sensing volume, a portion of which will correspond to a sample volume 533 that includes a sensing height 700 (defined as the distance between the sensor end and the particle in the fluid sample interacting with the incident light) and a nominal light path from the light source 702 and corresponding scattering by and/or fluorescence light path 704 of particles in the fluid sample. Accordingly, nominal optical path length is the sum of the length of 702 (light path from optical source to sample) and 704 (light path from sample to detector window).

Figure 7A:
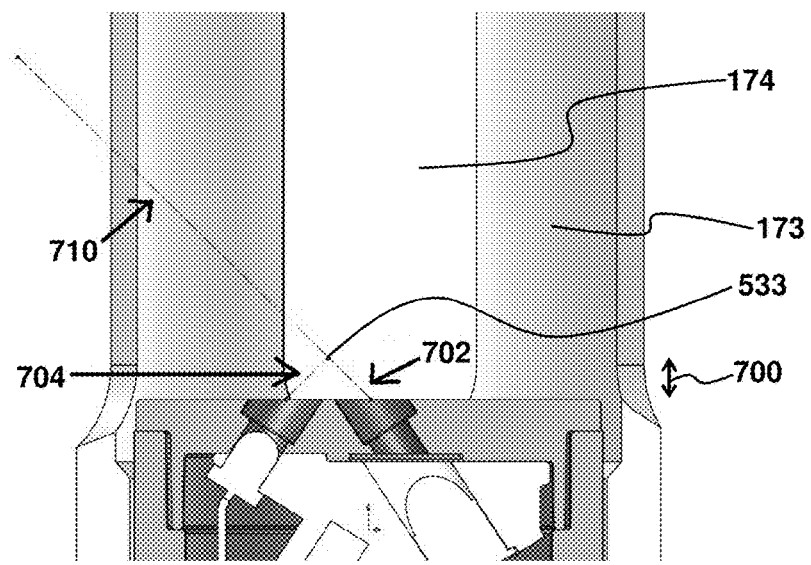
FIG. 7A illustrates use of a turbidity sensor with the guard of FIG. 6A with light scattering from the guard inner surface dependent of the orientation of the guard passages relative to the optical components.
Figure 7B:
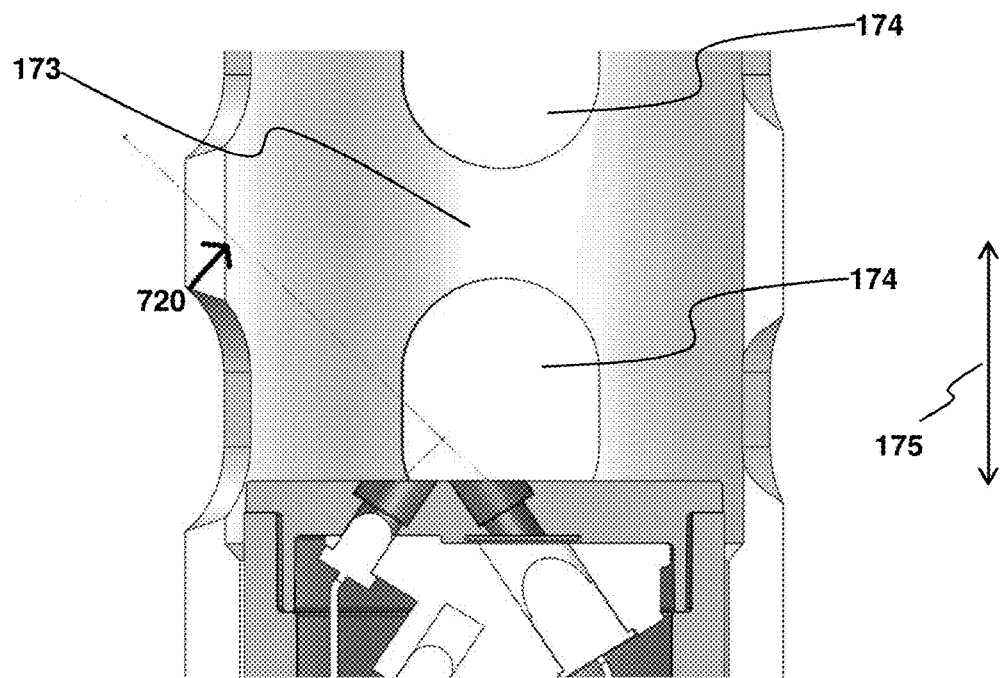
FIG. 7B illustrates an alternative guard design, where each of the passages of FIGS. 6A and 7A are provided as two separate passages separated by a passage separation distance, to provide constant optical characteristics independent of the guard passage orientation, for example, consistent background scattering.

One potential disadvantage of the guard configuration of FIG. 6A is illustrated in FIGS. 7A-7B. FIG. 7A illustrates that stray light scattering direction will be inconsistent, depending on whether stray light hits: a passage 174 and exits the guard; or a solid section 173 and is reflected back toward the sample volume with an opportunity to interfere with a true light scattering event. This inconsistency depends on the relative position of the guard to the detector and light source. This can be avoided, such as shown in FIG. 7B, by configuring the passages to ensure there is a consistent solid guard portion irrespective of the relative position of the guard. One manner in which this may be achieved is by providing a constant solid guard portion at a user selected distance 175. Accordingly, in an aspect any of the sensors provided herein may be configured to connect to a sensor guard having a uniform reflecting surface at a scattering separation distance 175 from the sensing surface. Adjacent to the scattering separation distance, a top fluid passage and a bottom fluid passage may be positioned to ensure good fluid contact and convection between the sample volume and the liquid outside the guard. Each of the plurality of individual passages 174 may be further divided into a pair of passages separated by a separation distance. In other words, each of the passages or openings 174 illustrated in FIG. 6A can be split into a pair of passages, such as the two passages 174 of FIG. 7B. Use of passages comprising a plurality, such as two individual paired passages separated by a separation distance, can provide light characteristics that are independent of sensor guard orientation.

Referring to FIG. 7A, region 710 of the guard illustrates that stray light can either hit the metal guard or pass through the passages 174. This difference in optical characteristic makes it not possible to predict the amount and direction of scattering from external surfaces, and further may change depending on the orientation of the guard. FIG. 7B, in contrast, is configured to have a constant solid guard portion 173 over the entire circumference, while still ensuring sampling of liquid via the passages 174. In this configuration, stray light consistently hits the inner surface of the guard as indicated by region 720, thereby providing a consistent optical characteristic, such as a consistent background scattering effect. Furthermore, unwanted light from outside the sonde that interacts with the detector is minimized. In this manner, optical characteristics are independent of the relative position of the guard.

Other opto-electronic components are operably connected to provide desired functionality and control, including any of those components described in U.S. Pat. Nos. 8,488,122, 7,142,299, 7,470,917, such as microcontrollers, electronic and integrated circuits, supply and associated electrical connections.

Example 4: Sensor Characterization

Figure 8:
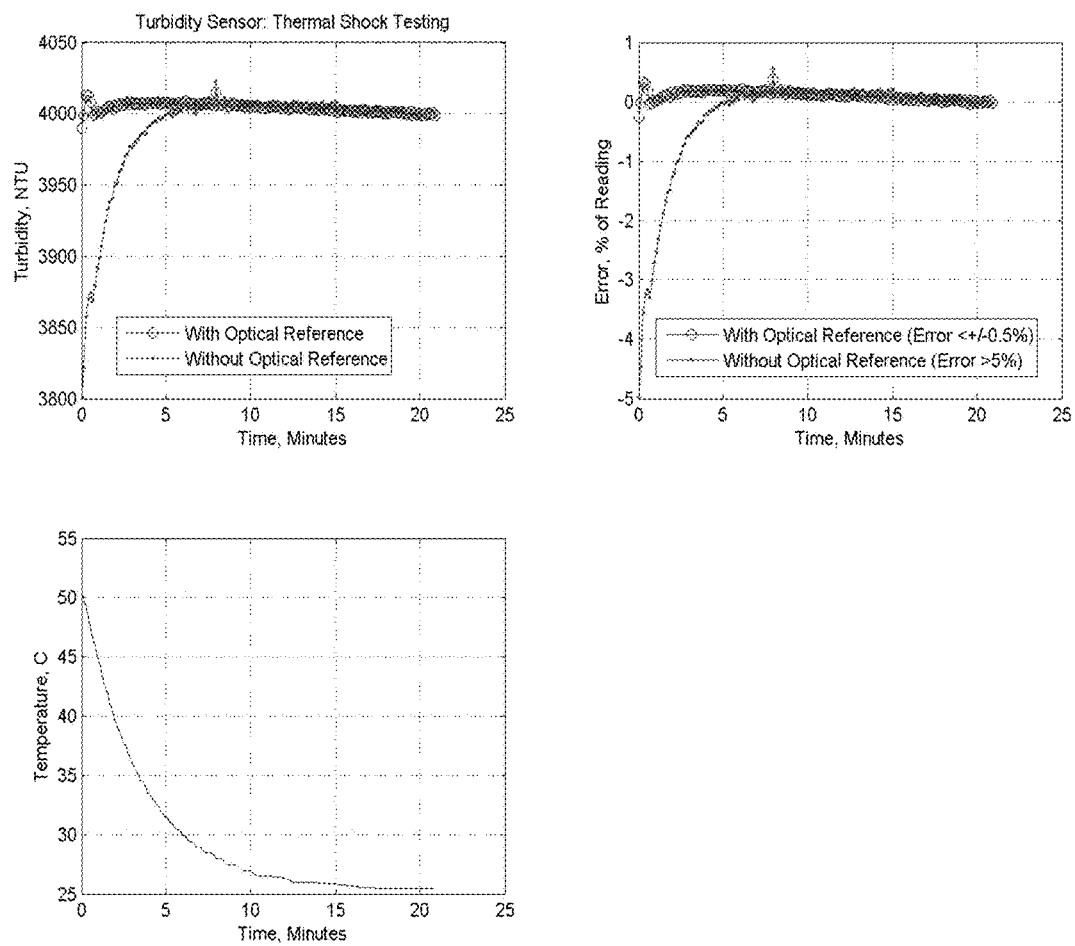
FIG. 8 summarizes the results of a turbidity sensor thermal shock test for a turbidity sensor with the reference detector (open circles) and without a reference detector (solid dots) at a turbidity level of 4000 NTU. The lower left panel illustrates the sensor temperature as a function of time. The top left and right panels are plot of measured turbidity and error percentage as a function of time.

FIGS. 8-12 are plots that characterize turbidity sensor performance. FIG. 8 illustrates the substantial improvement achieved by use of a reference detector to compensate for change in temperature. The sensor is heated to 50° C. and placed into a sample having a turbidity of 4000 NTU and allowed to cool, and turbidity measured as the sensor cools. The plots for the sensor having an optical reference to compensate for change in light output with temperature are significantly improved compared to a sensor without the reference detector. The reference detector compensation, such as by the ratiometric measure of detected light provides an error in turbidity measure of less than about 0.5%. In contrast, without such a reference detector, the error is greater than 5%. There is observable improvement in turbidity measurement for a change in temperature that is about 5° C. or more (compare the results at t=5 minutes or less).

Figure 9:
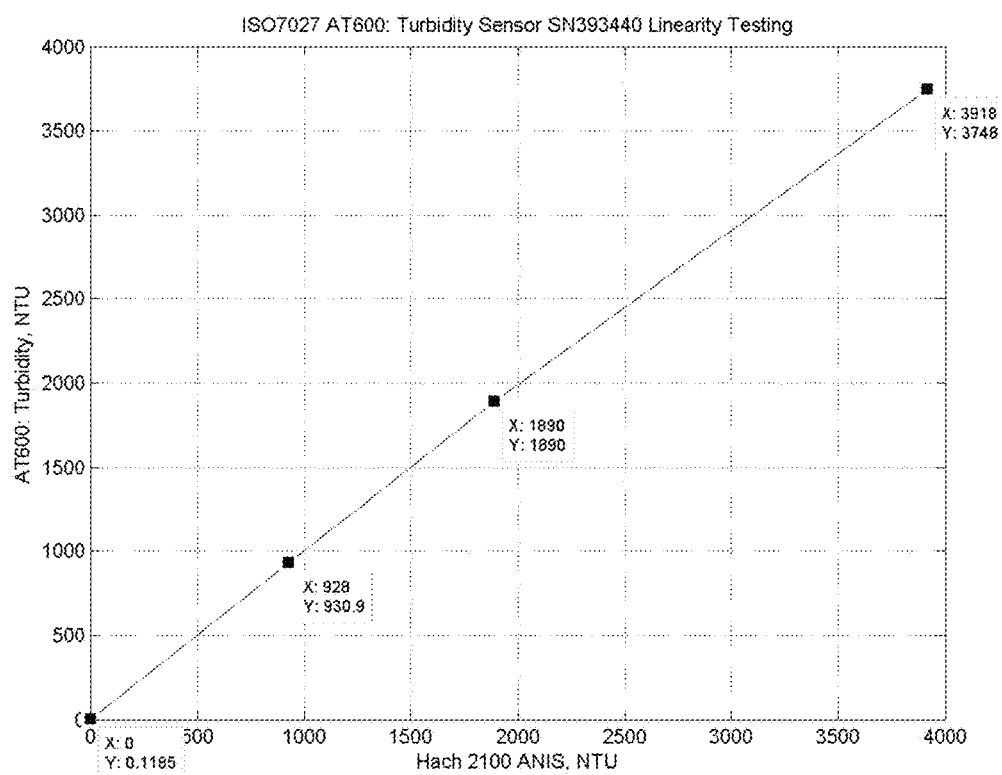
FIG. 9 summarizes an ISO7027 turbidity sensor of the present invention linearity compared to a conventional benchtop analyzer.
Figure 10:
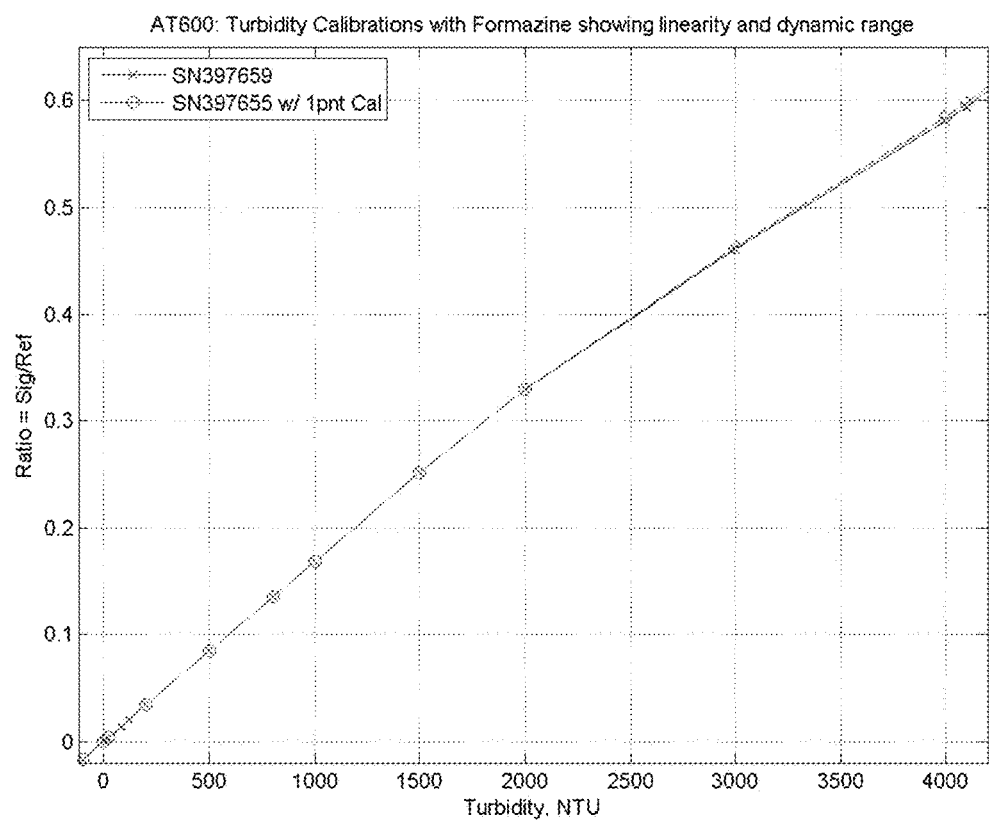
FIG. 10 is an ISO7027 turbidity sensor of the present invention calibration curve with formazine demonstrating good linearity over a large dynamic range of turbidity.
Figure 11:
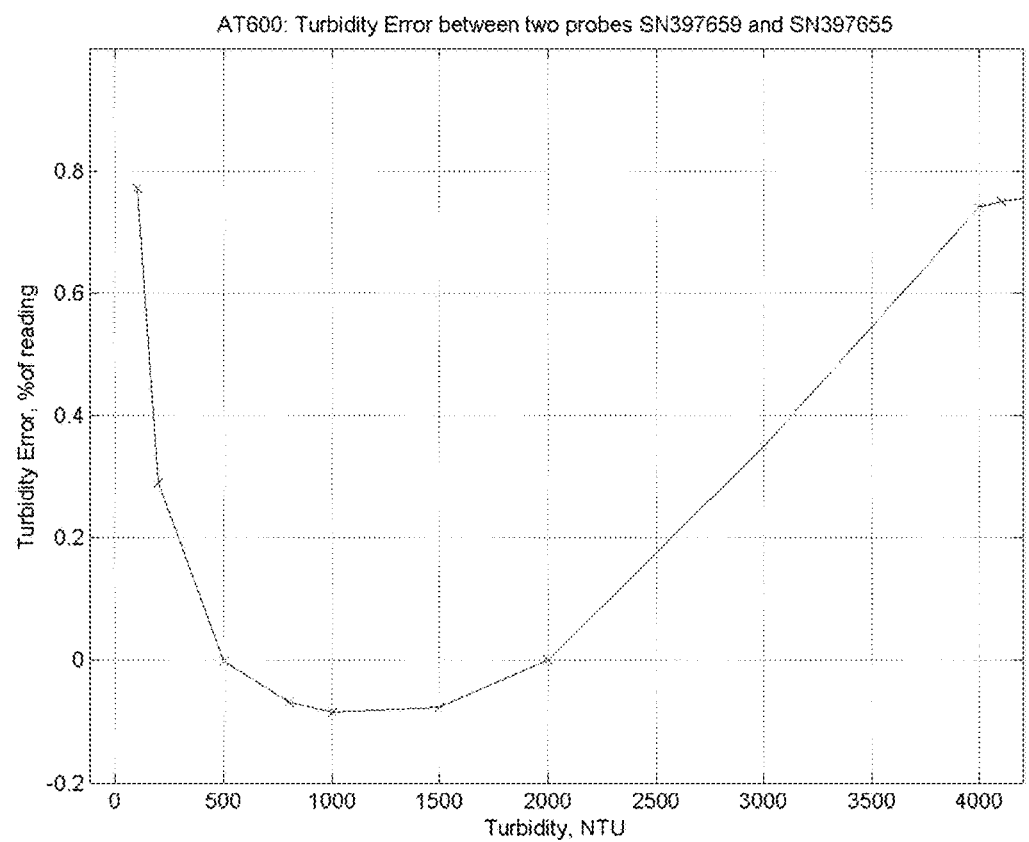
FIG. 11 is an ISO7027 turbidity sensor of the present invention plotting percent turbidity error as a function of turbidity over a dynamic range of more than 4000 NTU.
Figure 12:
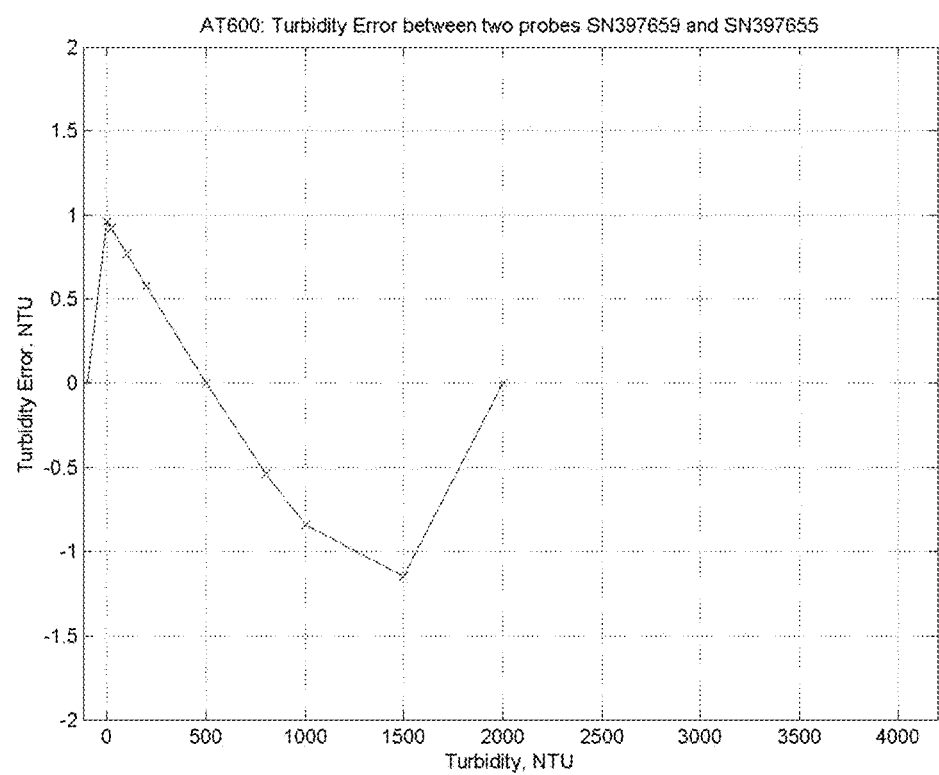
FIG. 12 is an ISO7027 turbidity sensor of the present invention absolute turbidity error as a function of turbidity over a dynamic range from 0 NTU to about 2000 NTU.

The turbidity sensors provided herein exhibit good linearity over a wide range of turbidity. FIGS. 9-10 illustrates the sensor easily achieves a 4000 NTU dynamic range with good linearity, including when compared to a Hach® 2100 Anis benchtop turbidity analyzer. Accuracy of the turbidity sensors is also robust, as illustrated in FIGS. 11-12, with two sensors exhibiting substantially less than 1% difference over a dynamic turbidity range.

Example 5: Conductivity Sensor in a Multi-Parameter Sonde

A multi-parameter sonde may have pie shaped sensors that fill the entire sensor space of the multi-parameter sonde. Other sondes, in contrast, use mostly round sensors that have open space between sensors.

Figure 13A:
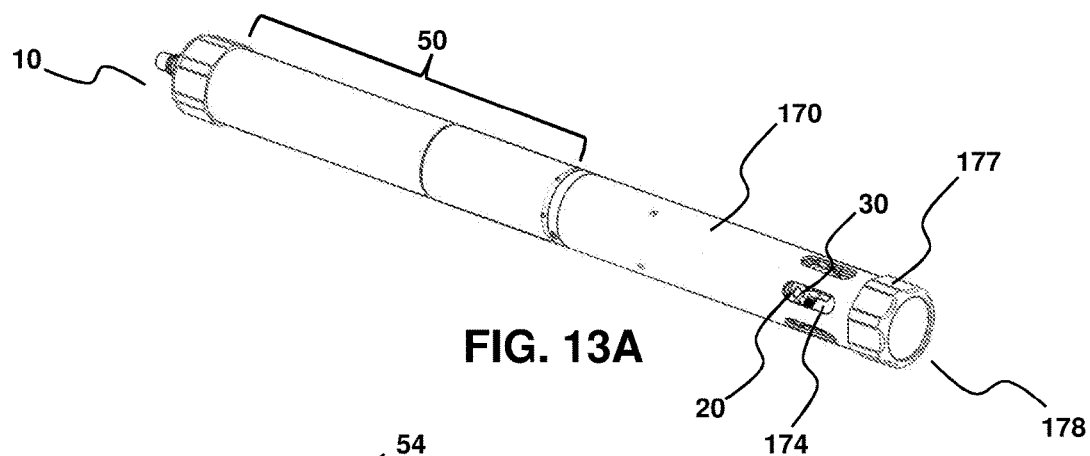
FIG. 13A is a top perspective view of a multi-parameter sonde with a sensor guard in a sensor guard configuration. 13B is a bottom perspective view thereof. 13C is a side view thereof.
Figure 13B:
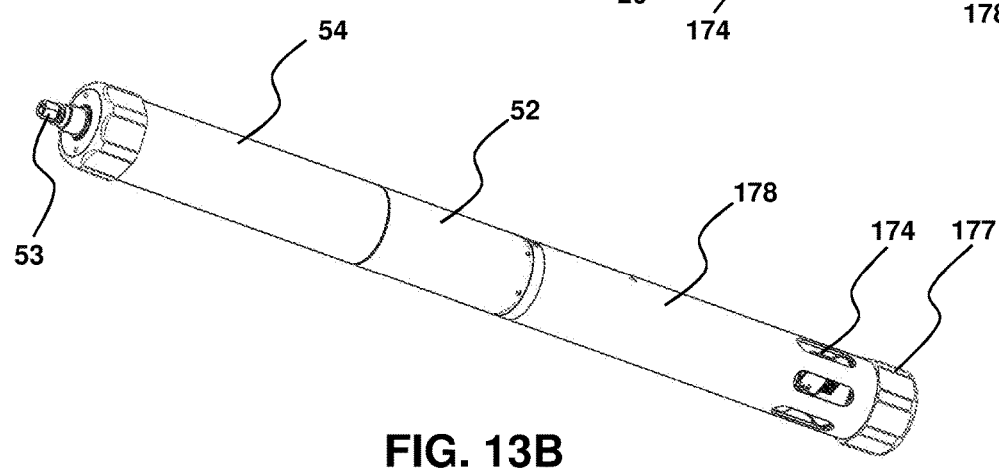
Figure 13C:
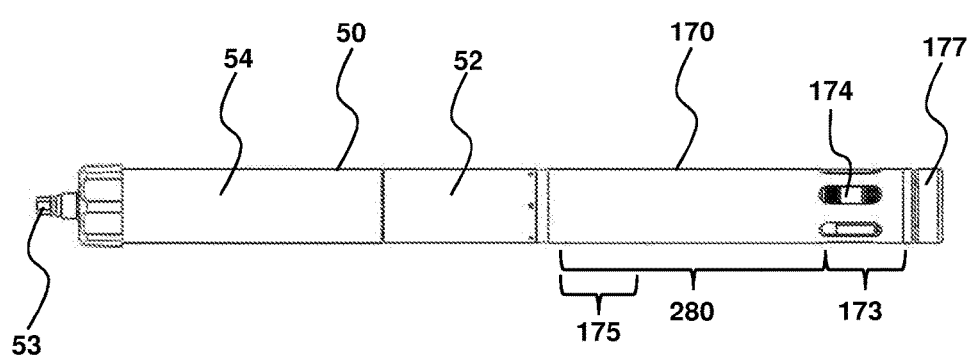

Referring to FIGS. 13A-13C, in a fully assembled configuration ready for sensing in a submerged environment, the multi-parameter sonde 10 has a plurality of independent sensors 20 disposed within a sensor guard 170, including any of the turbidity or fluorescence sensors described herein. The sonde is shown in a sensor guard configuration 178 in that the sensing end 173 having a plurality of fluid openings 174 is aligned with the distal sensing surfaces of each of the sensor. Covering end 175 is positioned in a proximal position, relative to the sensing end 173 of the sensor guard. The sensing end corresponds to the sample volume. The sensor guard is open-ended, with one end, the proximal end, closed via the connection with the base 50 and the other end, the distal end, closed via the cap 177. Sensor receiving volume 280 corresponds to the portion of the sensor guard 170 in which the sensors extend and, therefore, depends on the sensor longitudinal length. The volume of sensing volume 173 may be about 40 mL-50 mL, or about 46 mL.

The base 50 may further comprise a display portion 52 for indicating sonde and sensor status, and a base end 54 for containing other sonde components, such as power supply, electronics and external connection port 53. Those sonde components operably connect to the opto-electronics of the presently described turbidity and fluorescent sensors.

Figure 14A:
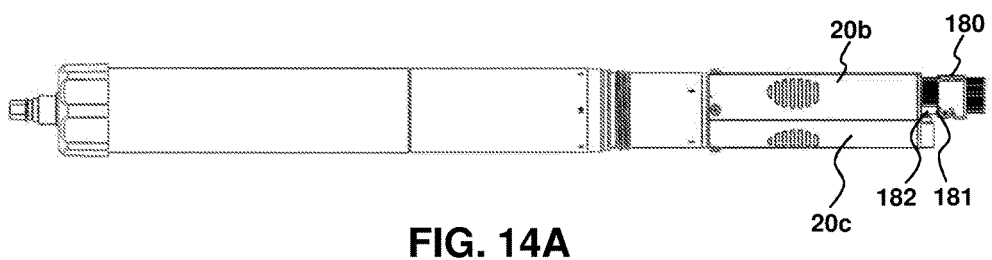
FIG. 14A is a side view of the multi-parameter sonde of 13A with the sensor guard removed to show the plurality of sensors that are in an adjacent configuration and a cleaning brush that are normally confined within a sensor guard during use. 14B is a perspective view thereof.
Figure 14B:
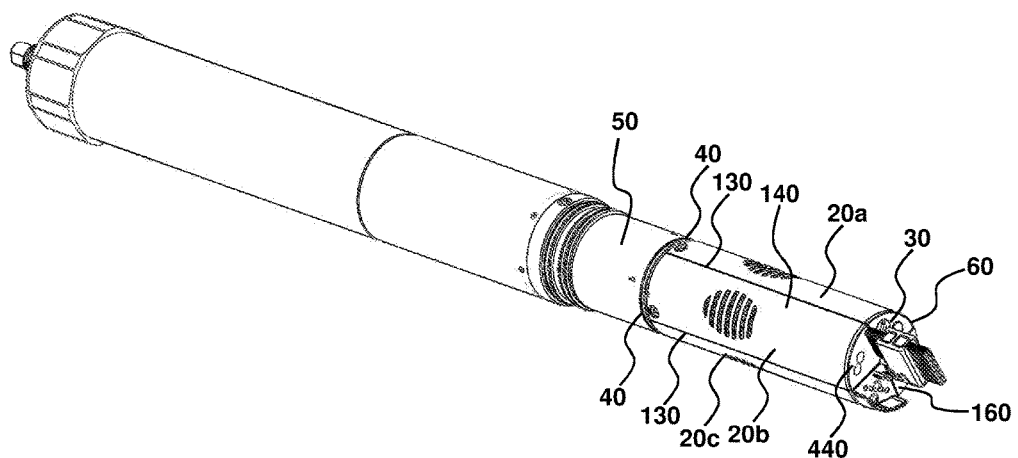

The multi-parameter sonde of FIG. 13A with the sensor guard 170 removed is illustrated in FIG. 14A-14B. Plurality of independent sensors 20 (20a 20b 20c 20d) (shown as sensor blank 160)) each have a distal sensing surface 30 and a proximal end 40 connected to the base 50, including in particular a distal sensing surface 440 of a turbidity or fluorescent sensor (corresponding to 20b). As shown in FIG. 14B, adjacent distal sensing surfaces contact each other to form a continuous distal sensing surface 60 having a substantially planar surface. The fitting between the independent sensors is so tight, that the outer surface cross-section visually appears as a solid circle. Because the fit between all the adjacent sensors is close or tight, the sensors are also referred herein as having a high "form factor", with minimal void volume or dead space between the sensors that extend from the base 50 and proximal end 40 to the distal sensing surface 30 and, in combination, the continuous distal sensing surface 60. Also illustrated is a wiper or brush 180 that is connected to a distal end 181 of a drive shaft 182.

Figure 15A:
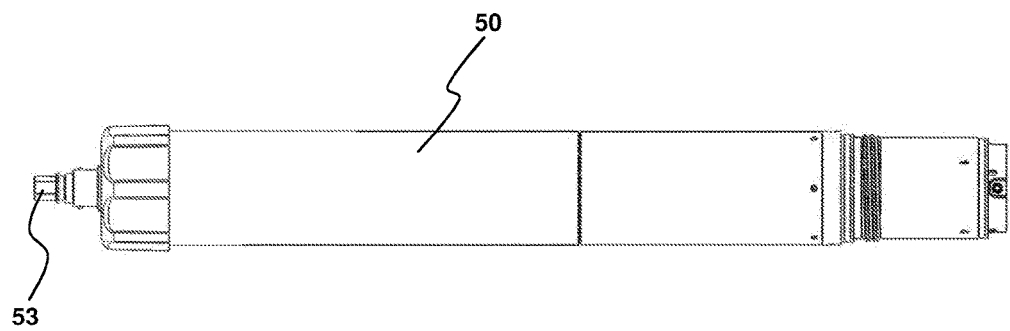
FIG. 15A-15B are illustrations of a base of the multi-parameter sonde, with the sensor guard, plurality of sensors, and central drive shaft removed, from a side and perspective view, respectively.
Figure 15B:
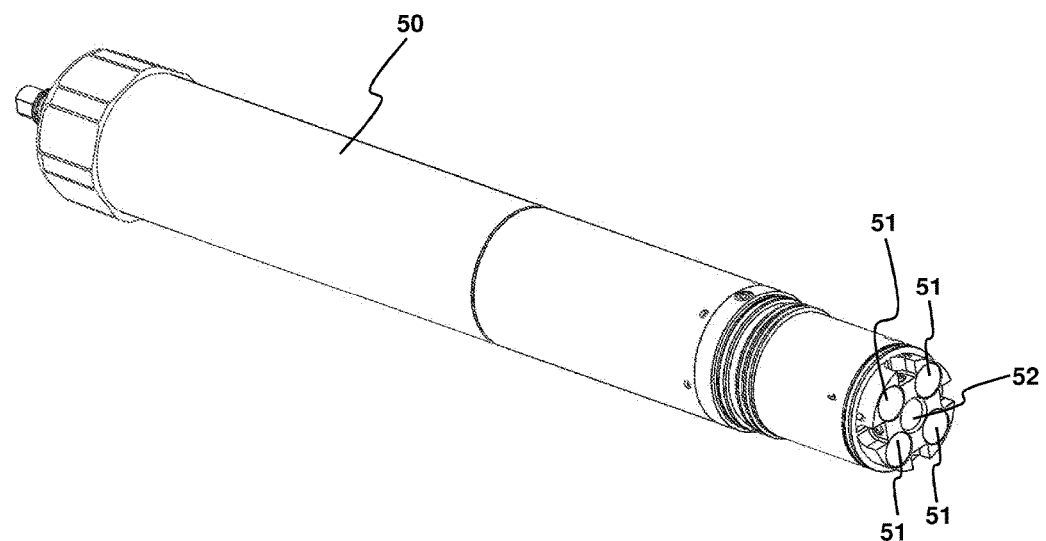

Referring to FIGS. 15A-15B, the sensor base 50 is shown without the sensor guard, the sensors, or the central support. Sensor ports 51 are configured to receive a proximal portion of the sensors, including a fastening member 88 shown in FIG. 2B. In the illustrated embodiment, four ports are shown for receiving four independent sensors, or a combination of sensors and sensor blanks having the same shape of the sensor. The blank sensor is useful for embodiments where not all sensors are needed and that, instead of occupying the space with an unused sensor, a relatively cheap blank may be used so as to maintain the many advantages described herein. Central support port 52 may be used to operably connect central support and attendant drive shaft extending therefrom. The port connections provide a reliable connection in a manner that also ensures convenient removability. Sensor base may contain other components for sonde functionality, operability and control, including such as by connector 53 for connection to an external electronic device.

The instant single continuous sensing surface allows a sensor cleaning brush to wipe on a flat even surface, without open spaces between sensors. The brushes and wipers are more effective at cleaning because there is not deflection around the sensors due to the space between probes, as is currently found with conventional multi-parameter sondes on the market.

FIGS. 16-17 are a close-up view of the wiper installed configuration and a wiper removed configuration. FIG. 16 shows an end-on view of the wiper 180 and distal surfaces of a four-sensor embodiment. In addition, the sonde has the capability to move the wiper brush 180° from the sensor it is currently reading. The sonde electronically detects the location of each probe installed from a unique resistor installed in the sensor. For sensors that are sensitive to the wiper brush's proximity, the brush moves to the opposite side during its measurement.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every combination of elements described or exemplified herein can be used to practice the invention, unless otherwise stated.

Whenever a range is given in the specification, for example, a size range, an angle range, or a time or a number range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:
1. A sensor for measuring turbidity comprising:
   a distal sensing end having:
      a vertex region;
      a first surface extending from said vertex region and ending at a first surface end point;
      a second surface extending from said vertex region and ending at a second surface end point, wherein said first surface and said second surface extend in different directions to form a vertex angle at said vertex region;
      a convex-curved outer surface that extends between said first surface end point and said second surface end point;
      a distal sensing surface defined by edges of said first surface, said second surface, said vertex region, and said curved outer surface; wherein a separation distance between said first surface end point and said second surface end point defines a maximum straight line distance on said distal sensing surface;
   a distal sensing end volume having a cross-section formed by said vertex region, said first surface, said second surface and said curved outer surface;
   an optical system positioned in said distal sensing end volume comprising:
      an optical source to generate a beam of electromagnetic radiation;
      an emission window through said distal sensing surface in optical communication with said beam of electromagnetic radiation and configured to pass at least a portion of said beam of electromagnetic radiation from said distal sensing end volume through said distal sensing surface to a sample volume adjacent to said distal sensing surface;
      a collection window through said distal sensing surface configured to pass at least a portion of an incoming beam of scattered electromagnetic radiation from particles suspended in fluid in the sample chamber in a collection direction to said distal sensing end volume; and
      a signal photodetector configured to detect said beam of incoming electromagnetic radiation in said collection direction;
   wherein said optical system is positioned in an optical plane that extends substantially perpendicular to said distal sensing surface and that is substantially aligned with a notional line corresponding to said maximum straight line distance.

2. The sensor of claim 1, wherein said optical system further comprises:
   a beam splitter positioned in optical communication with said optical source; and
   a reference photodetector to detect electromagnetic radiation reflected by said beam splitter.

3. The sensor of claim 2, wherein said beam splitter is comprised of a material selected from the group consisting of: sapphire, LASF9 glass, quartz, BK7, clear plastic, polycarbonate, cyclic olefin copolymer and acrylic.

4. The sensor of claim 2, further comprising an adjustable aperture optically connected to said reference photodetector to control light intensity to said reference photodetector.

5. The sensor of claim 2, wherein a ratio of light intensity detected by said reference photodetector and said signal photodetector compensates for a temperature-induced variation in optical output from said optical source, thereby providing temperature compensation without a temperature measurement.

6. The sensor of claim 2, wherein a ratio of light intensity detected by said reference photodetector to said light intensity detected by said signal photodetector is independent of light intensity generated by said optical source.

7. The sensor of claim 1, wherein said distal sensing surface has a surface area that is less than or equal to 4 $cm^2$ and said maximum straight line distance is greater than or equal to 2.3 cm.

8. The sensor of claim 1, wherein said distal sensing surface has a surface area that is between 3.2 $cm^2$ and 3.9 $cm^2$, and said maximum straight line distance is greater than or equal to 2.5 cm and less than or equal to 3.1 cm.

9. The sensor of claim 1, wherein said vertex angle is greater than or equal to 30° and less than or equal to 90°.

10. The sensor of claim 9, wherein said outer surface has a radius of curvature.

11. The sensor of claim 10, wherein said radius of curvature is less than or equal to 3 cm.

12. The sensor of claim 10, wherein said optical system is positioned within 5 cm from said distal sensing surface.

13. The sensor of claim 1, wherein said optical source and said photodetector are configured to provide a sensing height from said distal sensing surface of between 1 mm and 3.6 mm and a sensing volume of between 10 $mm^3$ and 30 $mm^3$.

14. The sensor of claim 13, wherein said optical source and said photodetector are configured to provide a nominal optical path length between said optical source and said photodetector in water that is between 4 mm and 10 mm.

15. The sensor of claim 13, having a dynamic range that spans up to 10,000 NTU.

16. The sensor of claim 1, wherein said first surface and said second surface are flat-faced and said sensor is configured for insertion into a multiparameter sonde comprising a plurality of independent sensors, wherein the sensors in combination provide a substantially circular cross-sectional footprint.

17. The sensor of claim 16, wherein said vertex region comprises a notch for accommodating at least a portion of a drive shaft.

18. The sensor of claim 1, wherein said distal sensing end volume cross-section has a cross-sectional shape formed by:
   said first inner surface and said second inner side that are straight-line linear having a length that is greater than or equal to 1.5 cm and less than or equal to 3 cm, and form a vertex angle with respect to each other that is greater than or equal to 30° and less than or equal to 90°;
said outer surface having a shape that is curved; and
an interior-facing vertex side that is curved for accommodating a portion of a rotatable drive shaft.

19. The sensor of claim 1, wherein said optical source is selected from the group consisting of: a light emitting diode (LED), a laser diode, a fiber optic light source, and a miniature lamp.

20. The sensor of claim 1, wherein said optical source is a LED.

21. The sensor of claim 2, wherein said beam splitter comprises a top surface facing said emission window and a bottom surface facing said optical surface, wherein one or both of said top and bottom surfaces are coated with an optical coating layer.

22. The sensor of claim 21, wherein said optical coating layer is a thin film interference layer.

23. The sensor of claim 1, wherein said photodetector is a photodiode.

24. The sensor of claim 1, further comprising one or more optical filters for controlling wavelength of transmitted electromagnetic radiation.

25. The sensor of claim 1, comprising optical sources and detectors having integrated lenses, filters, or lenses and filters.

26. The sensor of claim 1, wherein said emission and collection windows comprise a window material having an index of refraction that is greater than or equal to 1.7 over a wavelength range between 820 nm and 900 nm.

27. The sensor of claim 26, wherein said window material is selected from the group consisting of: sapphire; LASF9 glass, clear plastic, polycarbonate, cyclic olefin copolymer, and acrylic.

28. The sensor of claim 26, further comprising a wedge window formed of a material having an index of refraction that is greater than or equal to 1.7 for a wavelength range that is between 820 nm and 900 nm, wherein said wedge window material is adhered to said emission window material or said collection window material.

29. The sensor of claim 26, wherein said window material covers both said emission window and said collection window.

30. The sensor of claim 29, further comprising an end cap through which said emission and collection windows traverse, wherein said window material forms a crevice-free connection with said distal sensing end to facilitate surface cleaning and minimize unwanted biological growth during use in a liquid environment.

31. The sensor of claim 30, further comprising a light trap connected to said end cap to attenuate unwanted internally reflected electromagnetic radiation.

32. The sensor of claim 1, further comprising:
a sensor guard operably connected to said distal sensing end, wherein said sensor guard comprises an inner surface having a black coating that defines said sample chamber;
a plurality of passages through said sensor guard for introducing a liquid sample to said distal sensing end;
wherein said guard inner surface and plurality of passages are configured to provide an optically uniform surface to minimize effect of guard orientation on an intensity of said beam of incoming electromagnetic radiation.

33. The sensor of claim 1, with a long-term stability characterized by a sensor output drift that is less than 0.5% per year.

34. The sensor of claim 1, wherein said surfaces of said distal sensing end are part of a sensor housing that is water-tight.

35. The sensor of claim 1, further comprising an encapsulating layer positioned over said distal sensing end.

36. The sensor of claim 1, having a dynamic range of at least 4000 NTU.

37. The sensor of claim 2, further comprising a block that is optically opaque to visible light in which said signal and reference photodetectors are embedded, further comprising a light path through said block to provide optical communication between said optical source and said signal and reference photodetectors.

38. A sensor for measuring fluorescence comprising:
a distal sensing end having:
a vertex region;
a first surface extending from said vertex region and ending at a first surface end point;
a second surface extending from said vertex region and ending at a second surface end point, wherein said first surface and said second surface extend in different directions to form a vertex angle at said vertex region;
a convex-curved outer surface that extends between said first surface end point and said second surface end point;
a distal sensing surface defined by edges of said first surface, said second surface, said vertex region, and said curved outer surface; wherein a separation distance between said first surface end point and said second surface end point defines a maximum straight line distance on said distal sensing surface;
a distal sensing end volume having a cross-section formed by said vertex region, said first surface, said second surface and said curved outer surface;
an optical system positioned in said distal sensing end volume comprising:
an optical source to generate a beam of electromagnetic radiation;
an excitation filter in optical communication with said beam of electromagnetic radiation to generate excitation light having an excitation band of wavelengths;
an optical window through said distal sensing surface in optical communication with said beam of electromagnetic radiation and configured to:
pass at least a portion of said beam of electromagnetic radiation from said distal sensing end volume through said distal sensing surface to a fluid sample volume adjacent to said distal sensing surface, wherein at least a portion of said excitation band of wavelengths is provided to said fluid sample volume;
pass at least a portion of emitted fluorescent electromagnetic radiation from fluorescent molecules suspended in said fluid sample through said distal sensing end volume;
an emission filter in optical communication with said emitted fluorescent electromagnetic radiation that passes light of a desired band of wavelengths;
a signal photodetector configured to detect said incoming light of the desired emission band of wavelengths; and
wherein said optical system is positioned in an optical plane that extends substantially perpendicular to said distal sensing surface and that is substantially aligned with a notional line corresponding to said maximum straight line distance.

\* \* \* \* \*